(12) United States Patent
Powell

(10) Patent No.: US 7,648,704 B2
(45) Date of Patent: Jan. 19, 2010

(54) DIAGNOSIS AND TREATMENT OF HUMAN DORMANCY SYNDROME

(76) Inventor: Michael Powell, 650 University Ave., #200, Sacramento, CA (US) 95825

( * ) Notice: Subject to any disclaimer, the term of this patent is extended or adjusted under 35 U.S.C. 154(b) by 326 days.

(21) Appl. No.: 11/975,216

(22) Filed: Oct. 18, 2007

(65) Prior Publication Data

US 2008/0089954 A1 Apr. 17, 2008

Related U.S. Application Data

(63) Continuation of application No. 10/444,845, filed on May 23, 2003, now Pat. No. 7,288,257.

(60) Provisional application No. 60/382,913, filed on May 23, 2002, provisional application No. 60/383,271, filed on May 24, 2002.

(51) Int. Cl.
*A61K 39/00* (2006.01)
*A61K 38/22* (2006.01)
*C12Q 1/00* (2006.01)

(52) U.S. Cl. .......... 424/198.1; 435/4; 530/380; 530/399

(58) Field of Classification Search .......... 424/198.1; 435/4; 530/380, 399
See application file for complete search history.

(56) References Cited

U.S. PATENT DOCUMENTS

| | | | |
|---|---|---|---|
| 5,158,978 A | 10/1992 | Rubin | |
| 5,342,788 A | 8/1994 | Kunst et al. | |
| 5,691,456 A | 11/1997 | Adamczyk et al. | |
| 6,087,090 A | 7/2000 | Mascarenhas | |
| 6,579,854 B1 | 6/2003 | Mitchell et al. | |
| 6,664,239 B2 | 12/2003 | Mitchell et al. | |
| 6,756,369 B2 | 6/2004 | Mitchell et al. | |
| 2003/0007941 A1 | 1/2003 | Cornelius et al. | |
| 2003/0228628 A1 | 12/2003 | Powell | |

OTHER PUBLICATIONS

Marshall TG, Marshall FE; Sarcoidosis Succumbs to Antibiotics-Implication of Autoimmune Disease; Autoimmune Rev. Jun. 2004; 3(4); 295-300.

Hannah V. Carey; Physical Rev. 83; Mammalian Hibernation: Cellular and Molecular Responses to Depressed Metabolism and Low Temperature; pp. 1153-1181.

*Primary Examiner*—Ruth A Davis
(74) *Attorney, Agent, or Firm*—D. Benjamin Borson

(57) ABSTRACT

New methods for diagnosis of human dormancy syndrome are provided. Human dormancy syndrome is characterized by elevated serum ratio of rT3/fT3 compared to a population of normal subjects from which subjects suffering from fibromyalgia, chronic fatigue, obesity, dementias including Alzheimer's Disease and related dormancy conditions are excluded, and the presence of one or more findings related to reduced activity including torpor, chronic fatigue, insulin resistance, dementias, obesity and the like. Treatment of human dormancy syndrome is directed toward increasing fT3 levels or decreasing rT3 levels, or both, using pharmaceutical and/or behavioral methods. Other conditions that are associated with HDS can also be treated using T3 therapy, with or without specific psychological, behavioral or pharmaceutical therapies.

11 Claims, 3 Drawing Sheets

Relationships between FM, PTSD and HDS

| Clinical Finding | FM | PTSD | HDS |
|---|---|---|---|
| Slow wave sleep impaired | yes | yes | yes |
| Irritable Bowel Synhdrome (IBS) | yes | yes | yes, low VIP |
| HPA dysregulation | yes | yes | yes |
| High CRH | yes | yes | yes |
| sympathetic hyperactivity | yes | yes | yes |
| CSF substance P | increased | increased | yes |
| pain perception | increased | increased | |
| serotonin | low | low | yes |
| prolactin | increased | increased | increased |
| growth hormone response | blunted | blunted | yes |
| oxytocin levels | low | low | yes |
| nitric oxide metab abnormal | yes | yes | yes |
| cerebral blood flow | centralized | centralized | yes |
| cognitive function | impaired | impaired | yes |
| orthostatic hypotension | yes | yes | |
| fatigue | yes | yes | yes |
| exercise intolerance | yes | yes | yes |
| mitochondrial impairment | yes | yes | yes |
| hypervigilance | yes | yes | yes |
| compulsivity | yes | yes | |
| detachment/dissociation | yes | yes | |
| depression/anxiety | increased | increased | |
| significant emotional trauma | yes | yes | N/A |
| impaired NK cell activity | yes | yes | yes |

FIGURE 1

Correlations of FM and Hypothyroidism

|  | FM | Hypothyroidism |
|---|---|---|
| Slow wave sleep impaired | yes (8,11) | yes (157,158) |
| IBS | yes (15,16) | yes (159,160) |
| HPA dysregulation | yes (19-22) | yes (161-163) |
| High CRH | yes (27,28) | yes (162-164) |
| sympathetic hyperactivity | yes (32-34) | yes (165,166) |
| CSF substance P | increased (39-41) | increased (167-169) |
| pain perception | increased (45-47) | ? |
| serotonin | low (51-53) | low (170,171) |
| growth hormone response | blunted (61-63) | blunted (172,173) |
| oxytocin levels | low (65,66) | low (174,175) |
| nitric oxide metab abnormal | yes (39,52,71) | yes (176,177) |
| cerebral blood flow | centralized (73-75) | reduced (178,179) |
| cognitive function | impaired (80-82) | impaired (180,181) |
| orthostatic hypotension | yes (87-89) | yes (182) |
| fatigue | yes (90-92) | yes (183) |
| exercise intolerance | yes (96-98) | yes (184) |
| mitochondrial impairment | yes (97,102,103) | yes (185,186) |
| hypervigilance | yes (104-106) | (?) |
| compulsivity | yes (15,110) | yes (187,188) |
| detachment/dissociation | yes (82,113) | coma possible |
| depression/anxiety | increased (116-118) | increased (189) |
| significant emotional trauma | yes (121-125) | N/A |
| impaired NK cell activity | yes (128-130) | yes (190,191) |

FIGURE 2

Effects of Dormancy on Physiological Systems

| Physiological Variable | Dormancy | Fibromyalgia |
|---|---|---|
| rT3 | high | high |
| T3 | low | low |
| Serotonin | low | low |
| Melatonin | low | low |
| Oxytocin | low | low |
| Prolactin | high | high |
| Substance P | high | high |
| HPA axis activity | high | high |
| Muscle weakness | yes | yes |
| Exercise intolerance | yes | yes |
| Memory impairment | yes | yes |
| low oxygen consumption | yes | yes |
| Female:male Predominance | yes | yes |

FIGURE 3

DIAGNOSIS AND TREATMENT OF HUMAN DORMANCY SYNDROME

RELATED APPLICATIONS

This application is a Continuation of U.S. patent application Ser. No. 10/444,845, filed May 23, 2003, now U.S. Pat. No. 7,288,257, issued Oct. 30, 2007, which claims priority under 35 U.S.C. §119 to U.S. Provisional Patent Application Ser. No. 60/382,913, filed May 23, 2002, and U.S. Provisional Patent Application Ser. No. 60/383,271 filed May 24, 2002, each application and patent is herein expressly incorporated fully by reference as if separately so incorporated.

FIELD OF THE INVENTION

This invention relates to methods for diagnosing and treating human dormancy syndrome, a constellation of conditions heretofore unrelated to each other, including fibromyalgia, autoimmune diseases, coronary artery disease, breast cancer, prostate cancer and Alzheimer's disease.

BACKGROUND

Fibromyalgia is known as a diffuse periarticular musculoskeletal pain syndrome, primarily affecting females (90%) and is associated with insomnia, cognitive impairment, fatigue and depression. Fibromyalgia is also known to be associated with elevated levels of substance P (SP) in the cerebrospinal fluid (CSF), decreased levels of serotonin (5-HT) and a hyperactive hypothalamic-pituitary-adrenal (HPA) axis. The pathophysiological mechanisms underlying fibromyalgia are unknown, and the condition is considered uncurable. Exercise, cognitive behavioral therapy and antidepressant medication have been shown to diminish the severity of symptoms in some patients, but most patients remain in an unremitting state of illness. Standard laboratory tests are normal for most patients having fibromyalgia, and there is no evidence for autoimmune disease. Interestingly, there is an association of fibromyalgia with a significantly higher incidence of childhood and adult physical and emotional abuse and/or trauma. However, these findings have not been reconciled until the discovery of this invention.

The hormone triiodithyronine (T3) is a product of the thyroid gland. T3 is synthesized in the thyroid gland and is released as thyroxine (T4). T4 is released from the thyroid gland in response to, among other things, a pituitary hormone, thyroid hormone releasing factor.

The hormone L-3,3',5,5',-tetraiodothyronine (L-thyronine or T4) is a product of the thyroid gland. T4 is an inactive hormone when it is released into the blood stream by the thyroid gland. As T4 circulates throughout the body, it is absorbed by cells. Once T4 is within a cell it is converted by one of three enzymes (deiodinases) into either the active hormone L-3,3'5,-triiodothyronine (T3), the inactive T3 competitive product L-3,3',5'-triiodothyronine referred to as reverse T3 (rT3) or the deactivated L-3,3'-diiodothyronine (T2). Type I deiodinase (D1) is responsible for plasma production of T3 and rT3 by deiodination of the outer ring 5' position iodine to form T3 or deiodination of the inner ring 5 position iodine to form rT3. Type II deiodinase (D2) is responsible for intracellular deiodination and it's activity is limited to outer ring 5' position deiodination to form T3 from T4. Type III deiodinase (D3) activity is limited to inner ring deiodination of T3 to the inactive T2 product. Types I and III deiodinases play a role in the inactivation of thyroid hormones through inner ring (5) deiodination of T4 to rT3 and T3 to T2. Type I and II 5' deiodinase affects the outer ring and transforms rT3 to T2 or T4 to T3. The majority of T3 is produced in the liver and kidney and released into the blood stream, although most cells have the capacity to convert T4 to T3 or rT3.

T3 is metabolically active and stimulates production of cellular energy, and generally is an activator of tissues and organs. T3 acts by diffusing into cells, where it interacts with a cellular protein which transports the T3 to the cellular nucleus. T3 then acts by stimulating gene transcription to produce messenger ribonucleic acids (mRNA) of certain genes. Translation of the T3-induced mRNA produces cellular proteins that promote cellular activation. In contrast, rT3 has opposing effects, at least partially by inhibiting the action of T3, by way of competitively inhibiting T3 nuclear receptors in cells.

Thus, the balance between the effects of T3 and rT3 can determine the state of cellular activation. In Euthyroid Sick Syndrome (ESS), conversion of T4 to T3 is inhibited and conversion of T4 to rT3 is elevated. According to the American Thyroid Association, this condition does not warrant treatment. The American Psychiatric Association recognizes the use of T3 for treatment of depression, and levels of T3 are often decreased in patients with depression, as well as patients with fibromyalgia. Patients with fibromyalgia can have elevated levels of rT3. Dormant animals have elevated rT3 levels.

The so-called "Wilson's Syndrome" is reported to be diagnosed in patients having rT3 and T3 levels, reduced body temperature, and clinical findings of arthritis, muscular and joint aches, elevated cholesterol and several other findings.

Dementias are important causes of morbidity in people suffering from one or more of a variety of underlying disorders. Typically, dementias present as decreased mental clarity, decreased memory and complaints of low energy levels, resulting in reduced physical activity. In some patients, dementias also present with depression.

Treatment of dementias has been limited by the lack of understanding of underlying physiological and pathophysiological mechanisms leading to decreased mental functioning. Treatment of dementias typically are relatively ineffective, and many patients suffering from dementia, especially the elderly, do not improve. This is especially true of patients suffering from Alzheimer's disease, which is progressive and ultimately can be fatal. Because of the paucity of effective therapies, intense efforts are taking place to understand the underlying causes of dementias, including that associated with Alzheimer's disease, and to provide effective treatments for such conditions.

Latasa et al. reported that the amyloid protein, a major constituent of plaques observed in patients with advanced Alzheimer's disease, is at least partially under transcriptional control by thyroid hormones, including triiodythyronine (T3). Latasa noted three isoforms of alternatively spliced-amyloid precursor protein (APP) mRNAs.

Belandia et al. (J. Biol. Chem. 273:30366-30371 (1998) reported that T3 can negatively regulate the expression of the APP gene in neuroblastoma cells. The hormone triiodithyronine (T3) is a product of the thyroid gland. T3 is synthesized in the thyroid gland and is released as thyroxine (T4). T4 is released from the thyroid gland in response to, among other things, a pituitary hormone, thyroid hormone releasing factor.

The hormone L-3,3',5,5',-tetraiodothyronine (L-thyronine or T4) is a product of the thyroid gland. T4 is an inactive hormone when it is released into the blood stream by the thyroid gland. As T4 circulates throughout the body, it is absorbed by cells. Once T4 is within a cell it is converted by one of three enzymes (deiodinases) into either the active hormone L-3,3'5,-triiodothyronine (T3), the inactive T3 competitive product L-3,3',5'-triiodothyronine referred to as reverse T3 (rT3) or the deactivated L-3,3'-diiodothyronine (T2). Type I deiodinase (D1) is responsible for plasma production of T3 and rT3 by deiodination of the outer ring 5' position iodine to form T3 or deiodination of the inner ring 5 position iodine to form rT3. Type II deiodinase (D2) is responsible for intracellular deiodination and it's activity is limited to outer ring 5' position deiodination to form T3 from T4. Type III deiodinase (D3) activity is limited to inner ring deiodination of T3 to the inactive T2 product. Types I and III deiodinases play a role in the inactivation of thyroid hormones through inner ring (5) deiodination of T4 to rT3 and T3 to T2. Types I and II 5' deiodinase affects the outer ring and transforms rT3 to T2 or T4 to T3. The majority of T3 is produced in the liver and kidney and released into the blood stream, although most cells have the capacity to convert T4 to T3 or rT3.

T3 is metabolically active and stimulates production of cellular energy, and generally is an activator of tissues and organs. T3 acts by diffusing into cells, where it interacts with a cellular protein which transports the T3 to the cellular nucleus. T3 then acts by stimulating gene transcription to produce messenger ribonucleic acids (mRNA) of certain genes. Translation of the T3-induced mRNA produces cellular proteins that promote cellular activation. In contrast, rT3 has opposing effects, at least partially by inhibiting the action of T3, by way of competitively inhibiting T3 nuclear receptors in cells.

However, there was no known link between clinical dementia and thyroid hormones, and the effects of thyroid hormones on dementias in patients remained unknown until the discoveries that underlay this invention.

SUMMARY OF THE INVENTION

Thus, one object of this invention is the diagnosis of human dormancy syndrome.

Another object of this invention is to provide effective therapy for conditions related to human dormancy syndrome.

Another object of this invention is to provide improved treatments for patients suffering from dementias associated with human dormancy syndrome, including Alzheimer's disease.

Therefore, to meet the above and additional objects, we have unexpectedly discovered that in patients suffering from dementias, treatment using thyroid hormones, including triiodothyronine (T3) can alleviate symptoms of dementia. The elevation of T3 can be either due to addition of exogenous T3, or to agents that increase production of endogenous T3. Additionally, agents that decrease rT3 or can inhibit the de-activation of T3 can also be useful. The improvement can be prolonged, and can result in remission of severe mental impairment, increased sense of well-being, increased physical activity and increased energy levels.

This invention is based on the new and surprising observation that several medical conditions including dementias, heretofore unassociated with each other have a common etiology and share common characteristics; herein termed "human dormancy syndrome" (HDS). HDS has been previously unrecognized because many conditions that can appear as part of HDS have been considered "normal" according to current diagnostic criteria. However, I have unexpectedly discovered that the population of individuals used to assess "normal" is heterogeneous, comprising individuals without any HDS-associated disorders, and individuals having conditions, now considered part of HDS, that are not "normal." Thus, diagnostic tests have not identified individuals having HDS within a group of subjects because the "normal" range encompassed the observations of those patients. Thus, many HDS-associated conditions have remained undiagnosed and untreated.

Thus, in general, HDS is characterized by chronic, stress-related disease states, in which abnormalities in Adrenocorticotropic Hormone (ACTH) or Corticotropin Releasing Hormone (CRH) levels in body fluids, such as blood, elevated rT3/fT3 ratio, and one or more symptoms including torpor, fatigue, elevated appetite, centripital obesity, insulin resistance, fibromyalgia, depression, dementias and/or other findings described herein below.

I have unexpectedly found that numerous pathophysiological conditions can be successfully treated using thyroid hormone therapy using T3 or other agents that reduce the formation of rT3 or increase the production of T3. Adjunct therapy can improve the effects of thyroid hormone therapy. Such therapies include behavioral, cognitive, pharmacological or other types of therapies.

BRIEF DESCRIPTION OF THE FIGURES

The invention will be described with reference to specific embodiments thereof. Additional aspects of the invention are described in the Figures, in which:

FIG. 1 depicts a Table showing relationships between fibromyalgia, post-traumatic stress disorder and human dormancy syndrome.

FIG. 2 depicts a Table showing relationships between fibromyalgia and hypothyroidism.

FIG. 3 depicts a Table showing effects of dormancy on physiological systems.

DETAILED DESCRIPTION

This invention is based upon the new understanding of common features of heretofore un-reconciled pathophysiological findings. Disparate medical conditions including fibromyalgia, depression, dementias, autoimmune disorders (lupus, scleroderma, myositis, vasculitis, rheumatoid arthritis, psoriatic arthritis, demyelinating disease), reflex sympathetic dystrophy, post traumatic stress disorder (PTSD), post-Lyme disease, chronic back pain, breast cancer, prostate cancer, disorders of lipid metabolism and others are now understood to be included within a newly described syndrome, herein termed "human dormancy syndrome" or "HDS."

Once a diagnosis is made, therapy for HDS-associated conditions can include T3 replacement, treatment with agents that promote T3 synthesis and/or decrease rT3 synthesis, raise dopamine, raise serotonin, physical therapy, occupational therapy, (psychotherapy, trauma recovery programs, inner critic therapy, inner child work, shame recovery work, Voice Dialogue programs) and agents which interact with the sympathetic nervous system such as beta-blockers or alpha-agonists to mediate the fight-flight mechanism that triggers HDS and peptide systems, including those associated with substance P, vasoactive intestinal peptide, neuropeptide Y, enkephalin, neurotensin, bombesin, cholecystokinin, pyruvate dehygrogenase, oxytocin, Agouti related protein (AGRP) AlphaMSH, melanocortin or melanocortin receptors, melanin concentrating hormone (MCH), ghrelin, pro-opiomelanocortin (POMC) derived peptide, uncoupling proteins (UCP), prolactin, deiodinase, antitrypsin, hepatocyte nuclear factors (HNF) lipoprotein lipase, apoprotein, growth hormone, PPAR alpha, insulin and leptin. The testing of or use of agents which interact with the products of, or the DNA from the human hibernation gene PDK-4 and PL are also included in HDS diagnosis and treatment.

The fetal state (and coma) are the deepest forms of dormancy humans can achieve. Body temp is not a concern in utero nor is cognitive ability or skeletal muscle function. It would be interesting to see if there is a loss of slow wave stage 4 sleep in utero and a compensatory increase in slow wave sleep after birth. Animals exiting hibernation show this increase in slow wave sleep after hibernation and a deficiency of slow wave sleep in hibernation. A loss of slow wave sleep was the first anomaly noted in patients with FM in 1975 and started researchers thinking that it could be a disease beyond simple neurosis and depression. The high rT3 in umbilical cord blood with normal rT3 in maternal blood is evidence that humans hibernate and probably all mammals hibernate in utero. This could be proven with animal studies.

The hyperarousal of the sympathetic nervous system, and chronic elevation of CRH is seen in post traumatic stress disorder (PTSD). Much is written about this physiologically complex, self-perpetuating disorder but the underlying pathophysiologic mechanism of PTSD remains unrecognized. Our description of Human Dormancy Syndrome explains the purpose of the behavioral and physical aberrations in PTSD. Dormancy preserves life by minimizing exposure to a hostile environment. The loss of stage 4 sleep and hypervigilance are not random features of stress, shallow sleep readies an animals for self-defense as does hypervigilance. The decreased oxytocin decreases attachment behavior and lactation that could threaten survival and it lowers nitric oxide production. Nitric oxide receptors appear to be designed for dormancy since a decrease in nitric oxide decreases the diameter of peripheral blood vessels, minimizing heat loss. Stress decreases free T3 and this decreases nitric oxide synthase RNA in peripheral epithelial cells as well as those blood vessels supplying the cortex. However, the low free T3 stimulates nitric oxide synthase RNA in the central portions of the brain. The centralizing of blood flow reduces circulation to the thinking brain and increases blood flow to the regions associated with basic survival (amygdala, septal region, brain stem). The elevated CRH and sympathetic nervous system activity are a ready fight-flight system. Researchers studying dormancy in bears comment on the difficulty of sneaking up on a dormant bear stating: "Hibernating black bears, particularly mothers with cubs, sleep lightly, and bear expert Roger Powell of North Carolina State University says he has never approached a den in which a resident bear was not watching him come." The increased production of a CSF pain sensory molecule, substance P, has been a puzzling feature of FM, and SP is elevated in PTSD as well. Disruption of stage 4 without other stressors can trigger FM in healthy subjects, and this poorly understood relationship between deep sleep and enhanced pain has been documented since 1975.

During dormancy, elevated sensitivity to the environment with heightened pain sensitivity would offer a survival advantage and a reasonable compensation for cognitive impairment caused by the altered brain blood flow to the thinking portion of the brain (cortex). Altered mitochondrial structure with reduced membrane permeability and lower oxidative potential slows cellular respiration. This reduces the caloric needs of the dormant bear to better endure starvation, but in PTSD and FM afflicted people reduced mitochondrial function compromises the function of every cell producing exercise intolerance and cognitive impairment. VIP levels are altered in dormancy to limit gastrointestinal motility during starvation and minimize gastrointestinal energy expenditure, while PTSD/FM patients complain of Irritable Bowel Syndrome (IBS) another condition with an unknown pathophysiologic mechanism. Serotonin levels decrease and melatonin levels decrease as brain function slows. Melatonin levels rise with exposure to sunlight, a trigger for the end of dormancy.

Dormancy prolongs survival and there are many ways to initiate dormancy. Lowering fT3, blocking nuclear T3 receptors, lowering serotonin, lowering melatonin, disrupting stage 4 sleep, chronically elevating CRH, dropping body temperature (anesthesia), cortisone elevation, increasing IL-6 levels (inflammatory disease), starvation all have the potential of triggering PTSD/FM and dormancy. Animals do not always enter torpor under duress, hummingbirds enter torpor throughout the day to conserve energy stores. Many mammals enter dormancy before food supplies are unavailable. Some speculate that putting themselves on ice is a a means to reduce their metabolic rate and postpone food gathering to reduce exposure to predators until it is necessary during the breeding season: "If lifespan is limited physiologically, hibernation may stretch that lifespan over more breeding seasons, increasing the potential lifetime reproductive output." The point is that dormancy is used throughout the year, even during the warm months. Female echidnas in Tasmania remain in hibernation 7 months out of the year. Dormancy is more prevalent in nature than was originally considered and it is a state that humans enter for periods that can last decades. Dormancy explains every physiologic parameter that has been studied in humans with PTSD and FM. It also explains the pathophysiology of the stress-related components of most other stress-related human diseases. FIG. 1 shows common features of fibromyalgia, PTSD and HDS.

I Dormancy and Hibernation

Dormancy and hibernation are understood in zoology to include a number of physiological processes including decreased body temperature, torpor, decreased metabolic rate, decreased pulmonary ventilation, decreased heart rate and a sleep-like mental state. Small animals, such as ground squirrels, certain birds, and others exhibit deep hibernation, in which body temperature approaches ambient temperature, pulmonary ventilation and heart rate decrease to very low rates, and the animal outwardly appears "dead." Other animals, including bears, exhibit various degrees of torpor or dormancy. The nomenclature for hibernation has been discussed by experts in the field for many years. Although the terms 'hibernation', 'torpor', 'dormancy' and 'carnivorean lethargy' are sometimes used interchangeably, the following distinctions exist. Lyman et al. in their 1982 textbook entitled: *Hibernation and Torpor in Mammals and Birds* suggest the following: 'deep hibernation' is applied to the condition in which the animal's body temperature of about 5° C. for a period of days or weeks. Deep hibernation is reserved for small creatures with exaggerated heat loss due to their large surface to mass ratio.

The term 'torpor' is applied to an intermediate type of hibernation in which "body temperature declines markedly, but not usually below 15° C.". Torpor describes the "long winter sleep of the bear" and brief periods of chilling seen in hummingbirds and mice. Lyman et al. also describe the torpor of bears as 'dormancy' and reference is made to Hock (1960) who proposed the term 'carnivorean lethargy' to describe the state experienced during the winter by bears, skunks, raccoons, and badgers. Little is known about this state. Bears who "den up" become somnolent, do not eat for 100 days or more, and they form a fecal plug in the rectum called a tappen. The slowing of gastrointestinal motility is an important aspect of torpor and deep hibernation.

Kayser's 1961 landmark textbook *The Physiology of Natural Hibernation* further defines the state of wintering bears: "We now understand the exact wintering conditions of the bear. [references omitted] show that only the female bear hibernates. She is in a state of dormancy and motionless with no deep hypothermia, for the snow melts on her fur. The male bears go on prowling about in the woods, even in winter."

This gender distinction can be important, and as described later, the medical conditions associated with HDS affect women more than men.

Kayser quotes Winterruhe (1933) who defines dormancy as a state resembling sleep that is not easily aroused to action, although capable of it. The condition of the bear during their sleep might be described as dormant rather than torpid, in the sense that they are rather easily aroused to action.

Recent studies on wintering Black bears (Harlow et al. Nature 2001) report that body temperature drops only 4° C. below normal and bears may den up for five to seven months of the year. They postulate that "skeletal muscle protein and strength can be conserved . . . by rhythmically stimulating the muscles." We suspect that such findings may apply to HDS since FM and PTSD patients frequently display a syndrome referred to as Periodic Limb Movement or Restless Leg Syndrome that is associated with low CNS dopamine levels. Recognition of HDS and the need to maintain muscle strength during dormancy sheds light on this heretofore unexplained phenomenon in humans with stress-related illness. Stirling in his text: Polar Bears (Ann Harbor Press, 1988) describes an active but metabolically slowed state during periods of non-feeding as "walking hibernation". Hissa et al. (Comp. Biochem Physiol 1994) documented a decrease of approximately 50% in Finnish brown bear total and free T3 levels in the winter months.

We propose that this state in bears is physiologically similar to that of HDS. In addition to many references confirming increased female propensity for dormancy in bears, a similar gender distinction is described in dwarf lemurs, a primate that stays in torpor for about three months. Muller (Am. J. Primatol. 1999) reports: Adult males emerge from torpor earlier than females and offspring, even though food is still scarce. Early emergence from torpor puts males at an energetic disadvantage and confers no advantage in terms of access to females. Males patrol their home range, probably to guarantee it's integrity for the coming active season and to secure the food supply for their families.

The mechanism, which allows females to enter deeper states of torpor than males may be associated with increased female sensitivity to changes in T3 and rT3 levels which directly influence cellular metabolism. Kohrle et. al. (Mol Cell Endocrinol 1995) reports that D1 mRNA levels and activity were higher after T3 stimulation in the anterior pituitaries of female as compared to male rats. Further, the effects of T3 acceleration were greater as the percentage of women participating in the study increased. The increased female sensitivity to fluctuations in T3 and rT3 levels is central to the pathophysiology of HDS, FM, CFS and more.

II Dementias

We have unexpectedly discovered that dementias, including Alzheimer's Disease can be considered part of HDS. Thus, methods of this invention for treating dementias include those based on use of thyroid hormones, which can result in the diminution or alleviation of clinical signs and symptoms of dementia, including those associated with early stages of Alzheimer's disease. Clinical findings in dementias can include decreased mental clarity, decreased memory and complaints of low energy levels, resulting in reduced physical activity. In some patients, dementias also present with depression.

Although the exact mechanism of the improvement in symptoms is not known with certainty, one hypothesis is that T3, the activated form of thyroid hormone, plays in neurologic function. T3 is known to activate nuclear receptors in the CNS increasing brain metabolism and neurotransmitter synthesis. Postsynaptic serotonin receptors and norepinephrine receptors are also decreased with T3 therapy, a finding that is observed in subjects responding to antidepressant therapy. One article describes the reduced beta amyloid production in cultured neuroblastoma cells (Latasa et al., cited above), otherwise there is no mention of T3 therapy for patients with Alzheimer's disease. This empiric trial in a patient with early Alzheimer's disease demonstrated that T3 not only can attenuate the slow progression of dissociation, fatigue, forgetfulness and cognitive dysfunction, but it can restore normal or even slightly above normal function for the patients' age. To my knowledge, this is the first report of T3 induced remission of early Alzheimer's disease.

III Light, Stress, T3 and HDS

Dormancy can be initiated by stress, cold, darkness, starvation, sleep deprivation and/or other factors. Influence of melatonin on peripheral thyroid metabolism is consistent with what one would expect from environmental stimuli during the winter. The pineal gland activity is directly stimulated by light entering the eyes. The pineal gland decreases production of melatonin when there is less light in the winter months and the clinical syndrome of Seasonal Affective Disorder is one that affects primarily females who become depressed during winter months. The condition is treated with light therapy. In keeping with the dormancy hypothesis, Brzezinska-Slebodzinska et al (J Pineal Res 1998) found that melatonin has a stimulatory effect on rabbit 5'-monodeiodinase (5'-D1) activity in liver, and kidney and 5'-D2 activity in brown adipose tissue. There is a corresponding increase in serum T3 and rT3 levels increases. They report that "the rise in the serum T4 was probably due to the stimulatory effect of melatonin on the secretory activity of the thyroid gland itself.". Nedvidkova et al. (Endocrin Res 2000) study thyroid and serotonin levels in anorexia nervosa patients (AN). Their results suggest that low serum levels of thyroid hormones in AN reflect a dysfunction of HPT axis in AN patients. Serum serotonin levels correlate positively with T3 levels. They also report that AN patients in recovery show increased conversion of T4 to T3 rather than to rT3. Melatonin is synthesized directly from serotonin. Serotonin levels are low during hibernation. In one study of animals, a serotonin blocking agent induced hibernation in chipmunks in summer.

Sleep Deprivation Alters T3 Metabolism

Previous studies found that in rat brain, type II 5'-iodothyronine deiodinase activity is extremely sensitive to stress. Sleep deprivation was used as the stressor in this study, which documented that 5'D2 was very sensitive to sleep deprivation. Other studies showed that sleep deprivation also induces significant and sometimes dramatic changes in 5'D-II activities and tissue concentrations of thyroid hormones. However, changes in deiodinase activities did not ensure stable tissue concentrations of T3, but were, on the contrary, in most cases accompanied by marked changes T3 levels in the tissue. (146)

Stress can activate the HPA axis resulting in release of cortisol, an adrenal cortical hormone. The effect of dexamethasone (a form of cortisol) on peripheral deiodinase activity was documented by Burr et. al. (Lancet 1976). They found that a single dose of dexamethasone resulted in reduced serum T3 concentration and raised serum rT3 concentration after 24 hours. They concluded that adrenal glucocorticoids may have a pathophysiologic role in modulating the peripheral metabolism of thyroid hormone in stress. Bianco et al. (Endocrin 1987) noted the same relationship with endogenous cortisol in rats stressed by restraint. In their study, serum T3 levels decreased while rT3 levels increased. Adrenalectomy or metyrapone treatment with replacement on non stress doses of cortisol prevented the alterations in T3 levels during stress. The rT3 so produced can block nuclear T3 receptors, and thereby can reduce synthesis of 5-HT and the related hormone, melatonin. Administration of melatonin is known to increase liver T3 synthesis by increasing 5'-D1 activity (Nedvidkova et al 2000), decreased melatonin would further contribute to a decrease in T3 synthesis.

Stress Decreases Peripheral Conversion of T4 to T3 and Increases rT3 Levels

Previous studies (Lancet 1976) noted that the steroid drug, dexamethasone resulted in reduced serum-3,3'5-triidothyronine (T3) concentration and raised serum-3,3',5'-triiodothyronine (reverse T3 or rT3) concentration." (148). Additionally, the rT3/T3 ratio was more elevated after surgery. Thus the severity of the stress induced by surgery may interact with the mechanism of peripheral T4 conversion." (Ann. Endocrinol. 1982: 149). Sexual differences were observed, in that plasma rT3 values were higher for females on the examination day than on control days. The plasma levels of T4 were similar in both sexes." (150).

Survival May be Linked to Higher T3 and Lower rT3 Levels

In children with meningoccocal sepsis, striking differences were observed between survivors and nonsurvivors. "In those who survived, the most important changes within 48 h were seen in a normalization of cortisol and ACTH levels, but without a circadian rhythm; a decrease of rT3 and an increase in the T3/rT3 ratio." (J Clin Endocrinol Metab 2000: 155). Furthermore, in a study of canine hemorrhagic shock, T3 improved survival by acting on cardiovascular receptors or via the hypothalamic-pituitary-thyroid axis and that exogeneous rT3 is detrimental during the stress of shock." (156)

Oxytocin levels can be decreased in dormancy syndrome, the HPA axis remains hyperactive, and SP levels can rise. The torpor that develops prior to true hibernation can be associated with increased appetite and centripital fat accumulation. Liver lipid metabolism can be affected by the drop in T3 levels, which can lead to increased synthesis of low-density lipoprotein (LDL) and total cholesterol, with a concurrent decrease in high-density lipoprotein (HDL). This shift in serum lipid composition toward low density products and hypertriglyceridemia can make serum lipids more available for oxidation and gluconeogenesis, and the fats so produced will tend to remain non-solid at the low body temperatures characteristic of dormancy. Additionally, insulin receptor synthesis can decrease as T3 decreases, and there is a trend toward obesity that is short-lived as the animal faces winter. The reduced insulin receptor number and sensitivity can reduce glucose utilization during dormancy and is associated with hyperinsulinemia.

Elevated prolactin levels and diminished androgen levels can reduce fertility during dormancy, and these changes normalize in the spring when the HPA axis hyperactivity decreases, and T3 levels rise. Activity of the vagus nerve (cranial nerve X) can be reduced, resulting in reduced gastrointestinal motility, diminished secretion of digestive enzymes, fluids, and hydrogen ions. Heart rate can be as low as 1-2 beats per minute in some deep hibernators. The hyperactive HPA axis can promote relatively shallow sleep, with loss of slow wave sleep that is found to rebound after dormancy subsides.

Peripheral circulation can be shunted away from peripheral areas, permitting peripheral temperature to drop without compromising central function, and synthesis of the vasodilator, nitric oxide (NO) can be reduced by rT3 by decreasing the synthesis of the mRNA for nitric oxide synthase. Mitochondrial permeability and function can be altered, along with alterations in tissue levels of magnesium and calcium ions. The flux of magnesium into the serum occurs during dormancy and this flux may be associated with low tissue levels of magnesium levels. Dormancy can be initiated by cortisol's activation of 5-D2, which increases rT3 levels, thereby producing a state of heightened pain sensitivity by increasing substance P levels. Other physiologic changes include hyperactive HPA axis, low vagus nerve activity, slowed gastrointestinal motility, shallow sleep, infertility, low basal metabolic rate, centripital fat accumulation, dyslipidemia, hyperinsulinemia, and memory impairment due to alternations in neurotransmitter synthesis. A sustained increase in 5-D1 synthesis and activity increases T3 levels ending hibernation and restoring the animal to its optimal metabolic state.

FM is not Due to Primary Hypothyroidism

Stress alters deiodinase activity, which decreases T3 and increases rT3. Reverse T3 competitively inhibits T3 from binding with and stimulating thyroid receptors in the brain, hypothalamus, pituitary gland, liver, muscle, and other tissues. If it is the inhibition of thyroid hormone from stimulating cell nuclei that triggers the physiological aspects of FM & PTSD, then there should be physiological similarities between FM/PTSD and primary hypothyroidism, a causally unrelated condition that produces morbidity and mortality by understimulation of thyroid receptors through T3 deficiency rather than T3 inhibition. Table 2 below shows common features found in fibromyalgia and hypothyroidism. Although there are similar clinical findings, because of the above distinction between the presence of excess rT3 in FM compared to primarily decreased T3 in hypothyroidism, there is little direct causal association of FM and primary hypothyroidism. Correlations of fibromyalgia and hypothyroidism are shown in FIG. 2.

Oxytocin enhances nitric oxide release (192), enhances attachment behavior (193) and inhibits stress response (194), and therefore can be a desirable adjunct therapy. Elevated rT3 can be found in hibernating animals, including squirrels, tortoises, and in bears during winter. Bears do not achieve deep hibernation, but rather, enter a quiescent state of torpor or dormancy, in which they can be aroused by environmental activities. Substance P levels are also elevated in hibernating species. Moreover, decreased serotonin levels are often found. In one study of animals, a serotonin blocking agent induced hibernation in squirrels in summer. Thus, dormancy appears to be highly correlated with fibromyalgia in people. A summary of these findings is presented in FIG. 3.

IV Human Dormancy

Humans have a hibernation gene (Andrews et al., 2002) (195). Other hibernating primates (e.g., fat-tailed lemurs) use the gene correctly, but humans in modern society typically do not slow movements, stop eating or exhibit other behaviors characteristic of hibernation. Rather, stresses of daily life or underlying pathophysiology can result in attempts to avoid hibernation behaviors. Moreover, the stress of fighting our impulse to hibernate only deepens the metabolic shift toward dormancy, thereby exacerbating the problems associated with HDS.

The concept of human dormancy is widely applicable to numerous disorders, which heretofore have not been associated with each other. Humans are designed to respond to acute and chronic stress differently and this is reflected in the biphasic T3 response. As previously discussed (151), acute stress in rats produces the up regulation of fT3 for the first two hours presumably for the "fight-flight response". When stress persisted beyond a 6-18 hour period a second response ensues with an increase in rT3 levels presumably for the "freeze response". The response persisted and T3 metabolism did not normalize throughout the 2 week study period. Thus, humans are designed to respond to stress by shifting into a metabolically blunted, survival mode.

The T3/rT3 system can communicate two fundamental messages: "on" and "off," although there are degrees of each. Catabolism is like "on", and anabolism is like "off." When a single message persists, the effect is that of shifting more toward non-dormancy or dormancy, depending upon which signal dominates. Dormancy is not only a state of energy conservation with blunted cellular and metabolic activity, but one that may transform CNS neurotransmitter synthesis conserving energy by slowing mental and physical activity in conjunction with increased responsiveness to environmental stress, mediated by hyperactivity within the HPA axis. This survival shift can affect every physiological system. Reverse T3 is a powerful "off signal" for cells producing changes in insulin receptors, lipoproteins, serotonin, melatonin, oxytocin, nitric oxide synthase and mitochondrial proteins. Meanwhile rT3 can be an "on signal" for nuclei that deepen the dormancy shift by increasing synthesis of prolactin, SP, and antidiuretic hormone (ADH). Additionally, alphaMSH and the melanocortin system are involved here and these are inhibited during dormancy while the AGRP and NPY activity increases. Gut motility decrease along with a decrease in CCK levels and VIP levels. Vagus nerve activity dwindles and so does cardiac and gastrointestinal activity. Hibernation is not sleep, and the image of a mammal with its body temperature a few degrees above freezing for three months should come to mind as we consider consequences of attempted human hibernation.

The high rT3 physiological state is a survival shift that is maladaptive in the long term. Because the adverse environmental conditions associated with twenty-first century life are rarely limited to a few months in the dead of winter, and rarely resolve with the coming of spring, it is not uncommon for a human dormancy shift to last for years or until the stress subsides. The consequences can be severe and there are implications for every system and for every field of medicine. In contrast with dormancy, Syrian hamsters are more 'nervous' than other species of hamsters or squirrels and seem to be poised for arousal from dormancy at all times. Animals with this nervous condition are termed "stressed hibernators" and this confirms that animals in dormancy are constantly reacting to internal and external stimuli while hibernating. It is not a restful sleep.

V Diagnosis of Human Dormancy Syndrome

Diagnosis of human dormancy syndrome can be accomplished using clinical history, physical findings, and chemical tests of urine, blood, cerebrospinal fluid (CSF) and/or tissues. Pertinent historical features include symptoms of persistent fatigue, cognitive impairment, weight gain, depression, alopecia, constipation, insomnia, sleep apnea, loss of libido, cold intolerance, exercise intolerance, addiction to stimulants, history of Raynaud's Syndrome, dislipidemia, atherosclerosis, syndrome X, peripheral vascular disease, type II diabetes, Alzheimer's disease (and other dementias), demyelinating disease, (muscle tension headache, migraine), fibrocystic breast disease, breast cancer, prostate cancer, ovarian cancer, other cancers, cholelithiasis, pulmonary artery hypertension, pulmonary fibrosis, COPD, asthma, systemic hypertension, infertility, fibromyalgia, chronic fatigue syndrome, chronic wide spread pain and other chronic pain states, and obesity. Additionally, autoimmune conditions such as lupus, scleroderma, rheumatoid arthritis, sarcoidosis, vasculitis, myositis, ankylosising spondylitis, psoriatic arthritis, reactive arthritis, Reiter's syndrome, Becet's and polymyalgia rheumatica. viral, bacterial and fungal infections, septic shock, pneumonia and other serous infections, narcolepsy, hypertension, liver disease, esophageal dysmotility, inflammatory bowel disease, renal disease, Parkinson's Disease and coma. Furthermore, impaired stage 4 sleep, irritable bowel syndrome, elevated CRH, elevated sympathetic nervous system activity, dysregulated HPA, low serotonin, altered nitric oxide metabolism and NOS activity, low oxytocin levels, mitochondrial impairment and structural changes with decreased membrane permeability, compulsivity, hypervigilance, dissociation, impaired natural killer cell activity, elevated CSF substance P levels, blunted growth hormone response during provocation testing, orthostatic hypotension, altered cerebral blood flow may also be associated with HDS.

Laboratory findings in HDS can include elevated serum rT3 and low serum T3 levels, elevated 5-deiodinase type II (5-D2) activity, decreased 5'-deiodinase type II (5'-D2) activity, increased mRNA for 5-D2, decreased mRNA for 5'-D2, increased 3,5,3'triiodothyroacetic acid, low CSF serotonin levels, low CSF melatonin levels and elevated CSF SP levels. Low serum and CSF oxytocin levels and abnormal citruline levels may indicate low peripheral nitric oxide production.

Many of the above laboratory tests can be carried out using fluids and/or tissues using known methods. Adrenocorticotrophic hormone (ACTH), SP, cortisol, neuropeptide Y (NPY), leptin, serotonin, HP 20, HP 25, HP 27, NP 55 and 5'-D2 and 5-D2 levels can be measured using immunologically based methods, such as radioimmunoassay, enzyme-linked immunoabsorbent assay (ELISA) methods. Mitochondrial uncoupling protein (UCP), HNF-1, HNF-2, HNF-3 and HNF-4 levels and α-2 macroglobulin, vasoactive intestinal peptide (VIP), α-1 antitrypsin, chymotrypsin, peptide TSKY and DK, NK-6 B and DSIP levels are measured using known methods. Additionally, exercise testing, measurement of basal metabolic rate are known.

According to some prior art criteria, normal ranges of TSH, T4, rT3 and T3 are as follows:

| | |
|---|---|
| T4: | 4.5 μg/dl-13 μg/dl; |
| TSH: | 0.4 μIU/ml-6.0 μIU/ml |
| rT3: | 100 pg/ml-500 pg/ml |
| T3 | 55 ng/dl-171 nl/dl |

Additionally, fT3 ranges vary depending on the source. Thus, nonstandardized fT3 reference ranges contribute to the problem of recognizing "true normal". Commercial laboratories define their own normal range and these can vary by as much as 66%. A list of fT3 ranges are shown below:

| | |
|---|---|
| Quest Diagnostics | fT3 230-420 pg/dl |

-continued

| Unilab | fT3 2.4-4.5 pg/ml |
|---|---|
| The Lab Report | fT3 1.5-4.1 pg/ml |
| Healthcare Clin. Lab | fT3 1.45-3.48 pg/ml |
| ARUP | fT3 2.2-4.0 pg/ml |

(our ratio data was derived using the Healthcare Clinical Lab reference range for absolute values).

According to this invention, however, the ranges above represent a mixture of "true" normal values, taken from normal individuals, and undiagnosed individuals having HDS or associated conditions. Thus, the ranges specified do not reflect the "true" normal human condition. Rather, because the "normal" ranges are so wide, many individuals suffering from HDS are undiagnosed.

Thus, according to this invention, a proper normal range can be obtained from non-stressed individuals. By comparing the rT3/fT3 ratio of patients with HDS with a true normal range, an elevated rT3/fT3 ratio can indicate the presence of HDS.

VI Treatment of Human Dormancy Syndrome

Because hibernation in all animals known to hibernate is reversible, conditions associated with HDS are also reversible. In general, therapy is aimed at returning the individual's physiological state to a non-dormant one. Thus, metabolites, hormones, vitamins, minerals, amino acids, or drugs in a manner designed to reverse, mitigate, or prevent the physiologic state of human dormancy may be useful.

Stress, endogenous cortisol and exogenously administered glucocorticoids (e.g., dexamethasone) can alter activities of 5'-D2 and 5-D2. Stress can inhibit 5'-D2 activity and can increase 5-D2 activity. Because 5-D2 can convert T4 to rT3, increasing 5-D2 activity can increase rT3 and can promote HDS-associated conditions. Conversely, inhibiting 5-D2 and increasing the effects of 5'-D2 can increase T3 production and decrease rT3 production. Such use involves using T3 is a fashion that does not suppress T4 synthesis are desirable. Thus, sustained release forms of T3 may be especially useful, as can be drugs that activate 5'-D2 and/or inhibit 5-D1 activity. One can appreciate that inhibitors of 5-D1, such as peptide, protein or small molecule inhibitors, as well as agents that decrease the transcription of 5-D1 DNA into 5-D1 nRNA, processing of that gene product to 5-D1 mRNA, or processing of specific 5-D1 mRNA into 5-D1 may be useful. Conversely, agents that increase the efficacy of 5-D2, increase 5-D2 gene expression, nRNA processing to mRNA, and translation of 5-D2 mRNA into active 5-D2 may be useful.

5'-D2 and 5-D2 expression is regulated, and concentrations of T3 and rT3 are tissue dependent. Nuclear T3 receptors can signal transduction of molecules in the mitochondria which control oxidative phosphorylation. Deiodinase activity can control neurotransmitter synthesis (Korhle 1966). Supplemental T3 can rapidly elevate 5'-D1, 5'-D2 and to a lesser degree, 5-D1. These findings correlate with increased T3 and rT3. Interestingly, 5'-D1 mRNA levels and 5'-D1 enzymatic activity were higher after T3 infusion in females, than in males (Kohrle 1995).

Additionally, agents that decrease the synthesis of or effects of 3,5,3'-triiodothyroacetic acid can be beneficial.

Additional agents include serotonin re-uptake inhibitors (SRIs) such as Prozac®, St. John's Wort, and other hormones including melatonin, testosterone, oxytocin, selenium, iodine, magnesium and nitroglycerin may also be beneficial. Agents that block the hyperarousal of the sympathetic nervous system such as beta-blockers or alpha agonists (clonodine and the like) or alpha antagonists (prazosin and the like). Stable hibernation is facilitated by an NMDA-type glutamatergic process and arousal from hibernation in squirrels has been produced by the non-competitive antagonist of NMDA-type glutamate receptor with MK-801, an anticonvulsant by Research Biochemicals. The use of such an agent for HDS could be useful. Any drug that would block the NMDA receptors in the midbrain reticular formation should arouse animals from hibernation and dormancy.

The use of dopamine enhancing drugs (Mirapex, Sinemet, bromcriptine and the like) to reverse the low dopamine component of dormancy can be valuable. Thus, the concomitant use of a two or more dormancy reversing agents may be effective. For example, a combination of medications that elevate T3, lower rT3, elevate dopamine, elevate serotonin, elevate oxytocin elevated nitric oxide production can increase therapeutic efficacy. Moreover, combination therapy including beta-adrenergic antagonists (e.g., propranolol), alpha-adrenergic antagonists, behavioral medicine, psychotherapy, relaxation training, biofeedback, acupuncture and exercise can also improve outcomes.

Treatment should be maintained until serum levels of rT3 and T3 return to the true normal range, until the ratio of rT3/fT3 returns to the true normal range, and until symptoms resolve.

VII Treatment of Dementias

Thus, one goal of thyroid therapy for dementias is to normalize the proper balance between the different thyroid hormones. Thus, if rT3 is elevated and fT3 is reduced, resulting in an elevated ratio of rT3/fT3 in a disease state, restoration to a more normal value can be desirable, and is associated with cognitive and behavioral improvement.

Additionally, agents that decrease the synthesis of or effects of 3,5,3'-triiodothyroacetic acid can be beneficial.

It can be appreciated that side effects of thyroid therapy can be monitored, and should be maintained at an acceptable level.

Additional agents that can be used as adjunct therapies include serotonin re-uptake inhibitors (SRIs) such as (±)fluoxetine (Prozac®), fluvoxamine, paroxetine, sertaline, (±) venlafaxine, St. John's Wort, and other hormones including melatonin, testosterone, oxytocin, selenium, iodine, magnesium and nitroglycerin may also be beneficial.

Additional behavioral and/or cognitive therapies can be can be applied in addition to thyroid treatments described herein.

Treatment should be maintained until clinical signs, results of cognitive tests, subjective self-evaluative criteria and/or serum levels of rT3 and/or T3 return to the normal range, and until symptoms improve. As it is known that therapy with T3 can be chronic, therapy can continue for long periods, and may continue for the patient's lifetime, or until symptoms resolve without the need for continuing therapy.

EXAMPLES

The examples and descriptions included herein are for purposes of illustration only, and are not intended to be limiting to the scope of the invention. All references cited herein are incorporated fully by reference.

Example 1

Values of rT3/fT3 in Normal Subjects and Patients with Fibromyalgia

A group of 5 normal, athletic, healthy females was selected based upon general fitness and levels of activity. Serum rT3 and fT3 were measured using standard methods. The average ratio of rT3 to fT3 was 4.18±1.08 (Standard Deviation). The standard error of the mean (SEM) was 0.48 (n=5).

A group of 23 patients with fibromyalgia had rT3 and fT3 levels measured using the same methods as for the group of normal individuals. The average ratio of rT3 to fT3 in this group was 6.9±4.48. The SEM was 0.93 (n=23). Therefore, patients with fibromyalgia have elevated rT3/fT3 ratios compared to normal subjects. The average increase in rT3/fT3 in patients with fibromyalgia was about 65%.

Example 2

Treatment of Human Dormancy Syndrome 211 consecutive patient charts were reviewed for response to treatment for dormancy. 51 of 211 did not follow up or participate with treatment and these patients were omitted from the study (24% attrition).

A trial of slow-release T3, oxytocin, and intramuscular (IM) MgSO$_4$ for approximately 3 months was tested to reverse dormancy among fibromyalgia (n=160). Response to treatment was measured by patient symptom self-rating on a 0-10 scale evaluating energy level, pain score and overall sense of well-being. Of the patients in the study, 16 of 160 (10%) failed to respond and the remaining 144 of 160 (90%) did respond positively to treatment.

Remission was defined as a 70% response or better (ACR 70)=66/160=41%. An inverse relationship was noted between patient stress level and response to treatment. Therefore, it is possible that the addition of psychological treatment for PTSD and low dose therapy using a beta-adrenergic receptor blocker may have further increased the remission rate.

Example 3

Clinical Study of a Patient with Alzheimer's Disease I

A patient, Ms. B, is a pleasant 86 year old female, who was initially evaluated and treated for polymyalgia rheumatica (PMR), which responded to conventional treatment with low dose prednisone, usually less than or equal to 5 mg daily. Her symptoms of PMR have relapsed twice over the past few years and always respond quickly to low dose prednisone. She enjoyed a remission from September of 1999 through April of 2000. Another condition unrelated to her PMR was the presence of a slowly progressive decline in "mental clarity and memory" as she described it, and a complaint of low energy, rated as a 2/10, with 10 being full energy. Her physical appearance was that of a woman perhaps 10 pounds over her ideal body weight; she was tired in appearance and had a blank distant stare most of the time. She would not converse with the front office staff and her mental acuity, although not tested with a neuropsychiatric exam, was clearly compromised. She answered questions in a delayed, dissociated manner, cooperative but having difficulty assessing her status or remembering enough to answer the clinical questions.

Ms. B was diagnosed as having early Alzheimer's disease. She was not complaining of depression, nor was there a source for situational depression. Thyroid studies carried out in May of 2000 revealed a low-normal serum free T4 level of 0.7 (0.6-1.6 ng/dl), a low-normal serum free T3 level of 1.77 (1.45-3.48 pg/dl) and a normal serum thyroid stimulating hormone (TSH) level of 0.87 (0.34-5.6 uIU/ml). Her sedimentation rate was 46 mm/hr and she denied symptoms of PMR, but had a 3+synovitis in the right ankle.

She received a one month tapering course of prednisone. When evaluated in July of 2001, her worst complaint was that of fatigue, there was no evidence of PMR and the ankle swelling had improved. Her sedimentation rate was 43 mm/hr. We discussed the possibility of starting an empiric trial of thyroid T3 (Cytomel) to potentially improve her energy level and perhaps improve her cognitive ability. We discussed her T3 level, which was on the low side of normal. In October of 2001, she returned to clinic and a trial of T3 (25 mcg) was initiated after thoroughly discussing potential side effects of the medication. She tolerated the medication without complaints, and no significant improvement in energy level was reported until February of 2002. At that time she reported that her "brain was sometimes better and I have better energy." Her sedimentation rate was 18 mm/hr, her serum TSH level was 0.12 (0.34-5.6), her serum free T3 level was mildly elevated at 4.49 (1.45-3.48) and she was not taking prednisone. In April 2002, she described her energy level as a 6/10 and she appeared mentally more alert. Her pulse was 70 bpm and regular, there being no evidence of T3-induced tachycardia. She returned to the office in May of 2002, accompanied by her daughter, and she reported having an energy level of 8-9/10, and she described having "much improved energy and alertness," stating that she has been able to clean her home again and still have plenty of energy. She conversed with the front office manager for the first time in three years and she had a bright, mentally sharp affect that was remarkable. The transformation in her symptoms was dramatic and were was confirmed by her daughter.

Example 4

Clinical Study of a Patient with Alzheimer's Disease II

After our success with Ms. B, we sought to repeat the procedure using a pre and post treatment test called the Dementia Rating Scale-2 (DRS-2) from Psych Corp to quantify the response to T3 therapy. Our volunteer, Mr. S, is a 73 year old retired attorney with progressively worsening dementia who was diagnosed with Alzheimer's Disease by a neurologist. Mr. S had an older brother succumb to Alzheimer's disease and Mr. S was very concerned about becoming a burden to his family. He said that he had asked his neurologist why more people with Alzheimer's do not kill themselves when they realize they have such an awful, irreversible, terminal condition and the neurologist explained that most Alzheimer's patients are too unaware of what is happening to realize that they have a problem. Mr. S said he would not allow himself to get that far along. We discussed the possibility of T3 significantly improving his condition and he was eager to begin treatment. I had been treating Mr. S's arthritis for 14 months and on the day of his entry into this clinical trial he had forgotten the location of our clinic. His condition was worsening.

Mr. S was referred to a local psychologist for cognitive evaluation. The psychologist administered the DRS-2 and the results confirmed dementia with Mr. S's overall percentile score as 1 (out of 100)=severely impaired (see below) in Table 1.

TABLE 1

Pre-Treatment Clinical Findings

| Index | AMMS | Percentile | Interpretation |
|---|---|---|---|
| Attention | 9 | 35 | normal |
| Initiation/Preservation | 5 | 5 | severely impaired |
| Construction | 7 | 14 | marginal |
| Conceptualization | 5 | 4 | severely impaired |
| Memory | 4 | 2 | severely impaired |
| DRS-2 total | 3 | 1 | severely impaired |
| Age corrected | 1 | 1 | severely impaired |

Interpretation: Mr. S's pre-treatment profile is congruent with the diagnosis of dementia. His strength is in his ability to attend to external cue.

Mr. S's blood work showed a "normal" thyroid pattern with all values within the normal range: TSH=2.90 (0.34-5.60 uIU/mL), free T4=1.0 (0.6-1.6 ng/dL), free T3=2.43 (1.45-3.48 pg/dL), reverse T3 12 (10-24 ng/dL). The ratio of rT3/fT3=4.94.

Mr. S's medications had been stable for some time and included: Plavix 75 mg QD, Norvasc 10 mg QD, Diovan 80 mg BID, Flomax 4 mg QD, Sulfasalazine 500 mg 3 BID, Remicade infusion 3 mg/kg Q8 weeks, Fosamax 70 mg Qweek, Omega3 fish oil 3 gm QD, Prevacid 15 mg QD. The patient was accompanied by his wife who assisted with coordination of medication and clearly understood the T3 protocol her husband was about to begin. Slow-release T3 instead of Cytomel (instant release) was used for this study to reduce the potential for side effects. The T3 was compounded with methylcellulose to delay absorption and the initial dose was 7.5 ug BID and was well tolerated. His dose was increased to 15 ug BID the following week. His pulse and blood pressure remained stable, and his body temperature measured by oral digital thermometer was often low at 95 degrees.

After three weeks of T3 he reported that he could now read more than 5 pages of a novel without having to go back and reread what was just read. This was a significant improvement. His blood work was repeated at his 3 week follow up visit while taking 15 ug BID. His results were all in range: TSH 2.73, fT4 0.6, fT3 2.64, rT3 12, and his ratio of rT3/fT3=4.55 (7.8% decrease/improvement in ratio). His dose of T3 was increased to 22.5 ug AM and 15 ug PM. He was again evaluated in 4 weeks and still complained of memory problems and some insomnia on T3. Klonpin 0.5 mg 1/2 PO Qhs was given for the insomnia. Pulse was steady at 80-85 bpm and blood pressure had decreased slightly to 110/78 (initially 130/82). His next visit was 4 weeks later and his vital signs remained stable. His dose of T3 was held at 22.5 AM and 15 ug PM. He was scheduled for a repeat of his DRS-2 testing and blood work for the 3 month visit. His blood work revealed normal range fT3 2.35 and an immeasurably low rT3 of <10, making a ratio of <3.8. His TSH was normal at 1.30 and fT4 was normal at 0.6. Our target ratio of <4.0 is what is seen in healthy athletes. The sensitivity of the rT3 measurement prevents us from calculating the ratio more precisely since the rT3 is often below the detectable level in healthy athletes and patients on T3 therapy. Mr. S reported that he could now read an entire novel and remember it without having to reread sections. His repeat DRS-2 confirmed our clinical suspicion in Table 2.

TABLE 2

Before and After Treatment Findings

| Index | AMMS pre & 3 mo | Percentile pre & 3 mo | Interpretation |
|---|---|---|---|
| Attention | 9----->13 | 35----->89 | improved |
| Initiation/Preservation | 5----->10 | 5----->50 | improved |
| Construction | 7----->10 | 14----->50 | improved |
| Conceptualization | 5----->10 | 4----->50 | improved |
| Memory | 4----->5 | 2----->4 | severely impaired |
| DRS-2 total | 3----->9 | 1----->35 | improved |
| Age corrected | 1----->8 | 1----->25 | improved |

Interpretation: Mr. S's profile has radically improved with treatment. The dementia is all but gone, and the remaining pattern is suggestive of an underlying depression. This is reflected in the solo decrement of memory function.

Mr. S reported that the first time he took the test he "could not make any sense of it, and the second time it all made sense."

At this time treatment continues and the DRS-2 will be tested every 3 months to monitor additional improvement. His initiation & preservation improved from the 5th percentile to the 50th, construction from the 4th to the 50th, his attention from the 35th to the 89th percentile. The response to therapy was dramatic and there are no other drug studies that show comparable improvement for patients with Alzheimer's dementia.

Treatment for HDS-Related Autoimmune Diseases

T3 and Lupus

Systemic Lupus Erythematosus (SLE) is a chronic rheumatic disease of unknown etiology which affects skin, lungs, heart, abdominal organs, joints, blood counts, kidneys, muscles and the nervous system. Lupus involves inflammation that injures the above organs and can lead to serious morbidity and mortality. SLE tends to affect females 9 times more often than males and it is especially active during the child-bearing years. Lupus is three times more common in African American women than in Caucasian women and is also more common in women of Hispanic, Asian, and Native American descent. There are several types of lupus: Discoid lupus is limited to the skin, Drug-induced lupus is caused by a reaction to drugs and resolves when the drug is discontinued, and Systemic Lupus Erythematosus involves various organ systems and is not limited to the dermal manifestations. The ACR diagnostic criteria for SLE require 4/11 of the following symptoms: malar rash, discoid rash, serositis, oral ulcers, arthritis, photosensitivity, blood dyscrasias, renal disease, (+)ANA, (+)dsDNA, neurologic disease. The spectrum of disease for SLE can range from mild to life-threatening and the condition usually has an intermittent course with flare-ups and periods of remission that are often unpredictable. Stress will often be associated with a worsening of SLE symptoms. The most common presenting symptoms include extreme fatigue, painful or swollen joints, unexplained fever, skin rashes, and kidney problems. The treatment of SLE varies depending on disease severity and manifestations. For mild disease involving joints and skin, NSAIDs and Plaquenil are the usual treatment. For more severe arthritis Prednisone and Methotrexate may be necessary to achieve remission. For those with internal organ involvement such as cerebritis, serositis or nephritis, Imuran or IV Cytoxan may be required. SLE can be seen as an overlap syndrome with a mixture of features of SLE plus Sjogren's or Scleroderma or Rheumatoid Arthritis. In these instances a classification as Undifferentiated Connective Tissue Disease (UCTD) or Mixed Connective Tissue Disease (MCTD) is invoked. There is a lower incidence of end-stage renal disease in UCTD and MCTD than there is in SLE. To date there are no treatment protocols that recommend the use of thyroid T3 (triiodothyronine) as primary or adjunctive treatment for SLE, Scleroderma, MCTD or UCTD. We report the effective therapeutic use of T3 in three cases of SLE.

Example 5

Treatment a Patient with Systemic Lupus Erythematosus

A 42 year old female with SLE was referred to our clinic for evaluation of acute polyarthritis involving her hands, wrists, knees and ankles following a case of upper respiratory tract infection. Her serum ANA was (+) at 1:1280 (very high), her white blood count (WBC) was low at 2600 (normal>4000), she was anemic with HCT of 32% (normal is >34%) and her dsDNA was (+), a finding that is 98% specific for SLE. She also complained of severe fatigue and Raynaud's syndrome. Her joint pain and swelling responded to treatment with prednisone and plaquenil, but she remained fatigued after 5 weeks of treatment. Her prednisone dose was tapered and she was treated with T3 25 ug BID plus plaquenil. Her Raynaud's symptoms (cold, blue fingers) and fatigue improved significantly, but her low WBC persisted. After 6 months of treatment with plaquenil and T3, her condition remained in remission without Raynaud's, joint swelling or pain, and her anemia resolved. Her energy level returned to normal as soon as the T3 was prescribed and she remained normal despite a busy work schedule. There were no flare-ups of SLE symptoms over the 6 month course of treatment and follow-up.

Example 6

Treatment of Autoimmune Disease I

A 34 year old female with MCTD with features of RA and SLE presented with extreme fatigue, acute polyarthritis involving the hands, wrists, ankles and heels, a (+)ANA of 1:1280, (+)dsDNA, (+) RF 22 (normal<10), malar rash, oral ulcers, photosensitivity, and greater than one hour of morning stiffness. She was treated with plaquenil and T3 45 ug QD and prednisone was avoided because of her history of fragile type I diabetes. Within 3 weeks she was feeling much better, a period too rapid to attribute to plaquenil which generally requires 6-8 weeks for a treatment response. Her energy level was excellent and she continued to work despite ongoing swelling in her right hand and wrist. Methotrexate (MTX) was started at month 5 at 10 mg/wk. By month 7 she was "feeling great" on MTX and T3 15 ug QD. Her joint swelling had resolved, her energy level was an 8/10, her pain a 0-1/10 and she continued to work without appreciable disability.

Example 7

Treatment of SLE II

A 68 year old female with SLE with erythematous facial rash, photosensitivity, pleuritic chest pain/Serositis, (+)ANA 1:640, (−)RF and ESR of 50 mm/hr (normal<20). She responded to treatment with prednisone and plaquenil and went into remission. She later developed a rash to plaquenil which was discontinued. Eight months later she developed diffuse muscle pain, and her ESR was very elevated at 104. Her WBC was low and a trial of Imuran was initiated along with prednisone. Her symptoms improved, but 2 months later she broke her ankle and Imuran and prednisone were discontinued. Her WBC remained low at 3700 and she was extremely fatigued. Eventually a trial of T3 was initiated for fatigue and in hope that her WBC would improve. Initially she received treatment with T3 25 ug with only partial response. Her muscle pain decreased when her dose was increased to 35 ug, and her symptoms completely resolved when her dose was increased to 60 ug QD. Her low WBC increased from 3500 to 9600, she reported no pain and was able to resume playing tennis.

The above Examples indicate that T3 can be used as adjunctive treatment for patients with SLE or MCTD, as treatment for fatigue and possibly the inflammatory manifestations of the disease. It was effective in place of prednisone and improved both red and white blood counts. Inflammation is known to decrease 5' D1 activity through IL-6 production, and this may explain, in part the positive effects of T3 therapy. Autoimmune diseases flare with stress, which also decreases 5' D2 activity, and this may explain the positive effects of T3 therapy. Autoimmune diseases tend to affect women more than men, and to date there is no explanation for the female predominance. Females are more sensitive to fluctuations in tissue T3 levels and enter hibernation and dormancy more efficiently than do males. HDS may explain the female predominance of autoimmune disease and the reversal of HDS may benefit those afflicted with these diseases. Here the influences of T3 also minimize the need for prednisone, a medication with many unpleasant side effects.

Treatment of Rheumatoid Arthritis

Rheumatoid arthritis (RA) is an inflammatory disease that primarily affects the joints and can also involve the eyes, lungs, heart valves and coronary arteries. It is often associated with premature death due to heart disease. RA is characterized by inflamed joints having symptoms that are in a symmetrical, bilateral distribution, with morning stiffness, swelling, fever, fatigue, anemia and occasionally rheumatoid nodules over the extensor surfaces of the body. The joint inflammation leads to erosions, which can lead to deformity and disability. The cause of RA remains unknown, but there is a genetic predisposition with HLA-DR4 surface antigens. RA is diagnosed by the ACR criteria which require 4 of the following: polyarthritis involving >3 joints, symmetrical synovitis, inflammatory distribution, morning stiffness lasting >1 hour, (+)rheumatoid Factor (RF), family history of RA, x-rays confirming erosions or juxtarticular osteopenia, rheumatoid nodule formation. Patients with the RF are referred to as "seropositive RA" and the 30% without a RF are referred to as "seronegative RA". Treatment options include NSAIDs, prednisone and disease modifying drugs (DMARDs) that slow the progression of disease and can lead to remission. DMARD's generally take a month or two for the therapeutic effects to be realized and there are 14 DMARD's available, each with its own side effect profile. They include methotrexate, leflunomide, D-Penicillamine, sulfasalazine, gold therapy, minocycline, azathioprine, plaquenil, cyclosporine, prograf, Remicade, Enbrel, Humira, and Anikinra. RA can present with other conditions in an overlap condition such as MCTD and it can present with Fibromyalgia. Fibromyalgia does not respond to treatment with NSAIDs, prednisone or DMARD's. The use of T3 for the treatment of RA has not previously been described.

Example 8

Treatment of Rheumatoid Arthritis I

A 71 year old female with seropositive RA (RF=65) and joint swelling in her hands, knees and feet. She was treated and partially responded to IM gold, a compound known to have many side effects including the ability to decrease T3 levels. She had also been treated with MTX which caused hair loss, and plaquenil which was ineffective. A trial of Imuran was poorly tolerated due to diarrhea and Arava did not adequately control her symptoms of joint swelling. Intermittent corticosteroid injection was necessary for control of her wrist swelling. She later developed diffuse muscle pain in a fibromyalgia distribution as fibromyalgia can coexist with RA and SLE. T3 therapy 30 ug QD was initiated and within 30 days her joint swelling decreased along with the complete resolution of her Fibromyalgia muscle pain. Atenolol was prescribed to control her pulse rate and feelings of activation by the T3. When the T3 was discontinued and T4 (synthroid) was reintroduced, her joint swelling and muscle pain returned. The T3 was reinitiated and her symptoms again remitted. She commented: "I never thought I'd feel this good again." She was able to travel again and reported being able to shop for 12 hours without flaring her condition. Such a complete response to treatment is rare for those with RA.

Example 9

Treatment of Rheumatoid Arthritis II

A 65 year old female with seropositive RA for 50 years and severely deformed hands and feet requiring multiple surgeries presented with severe fatigue, depression and joint and muscle pain that is not controlled on MTX 20 mg QWk. A trial of T3 25 ug QD has an immediate and dramatic effect with resolution of depression, fatigue, muscle and joint pain. She is able to taper her dose of T3 after 2 months and her symptoms remain in remission.

The potential benefit of treating the dormancy component of RA with T3 and other dormancy reversing agents holds great promise for patients with inflammatory disease. RA affects the lives of greater than 2 million Americans and it is one of the leading sources of disability. T3, a relatively inexpensive treatment with few potential side effects, appears to dramatically improve the quality of life of RA patients by restoring energy levels and diminishing muscle and joint pain and swelling. The use of T3 for the treatment of RA and other inflammatory arthritities has not been described until now.

Treatment of Post-Lyme Syndrome

Lyme disease (LD) is caused by a bacterial infection with *Borrelia burgdorferi* (Bb) transmitted by the bite of an infected tick. Bb infection can be associated with flu-like symptoms, severe fatigue, expanding red bulls-eye rash, arthritis resembling RA, nerve (Bell's palsy) and/or heart problems. Bb infection can also be asymptomatic and 14% of forestry workers in endemic areas test positive for infection with Bb. Diagnosis is based on clinical symptoms and blood or urine testing for Bb antigens and antibodies. For those who are symptomatic, the treatment depends on the severity of disease. For those with skin and joint symptoms, 2-3 weeks of doxycycline or minocin is usually curative. For those who have neurologic involvement or cardiac involvement (heart block), IV antibiotics are recommended for 1 month. There are patients who do not respond completely to the above treatments and continue to suffer from fatigue, cognitive impairment and pain and this syndrome has been referred to as Post Lyme Syndrome. It has been studied at various research centers and these studies offer contradictory results. Some researchers contend that Post Lyme Syndrome represents ongoing, partially treated infection that may remit with long term antibiotic therapy. There is more evidence supporting the contrary opinion that ongoing infection cannot be documented and that long term antibiotic treatment does not significantly alter the symptoms of Post Lyme Syndrome beyond what is seen with placebo. Our experience with inflammatory disease and HDS suggested a role for the use of T3 and other agents that reverse HDS. Below are Examples 9 and 10 documenting the efficacy of reversing the HDS aspects of Post Lyme Syndrome with T3.

Example 10

Treatment of Post Lyme Syndrome I

A 63 year old male presented with history of Bell's palsy, polyarthritis, extreme fatigue, (+) Lyme serology, (+) Lyme urine antigen, (–) RF. Treatment with minocin decreased headaches, but fever and chills persisted. Treatment of Babesia (an infection that is also associated with tick bite) resolved fevers and chills. Fatigue remained severe and patient fell asleep while driving. Treatment with T3 45 ug improved his energy levels and from 4/10 to 7/10 and decreased his pain from 10/10 to 2/10. Atenolol 25 mg 1/2 QD was used with T3 to control sympathetic hyperactivity associated with HDS and maintain normal heart rate. Patient was tapered off of T3 in 4 months and was still in excellent health four months later.

Example 11

Treatment of Post Lyme Syndrome II

A 57 year old female presented with Lyme disease after receiving multiple tick bites while working in the Sierra Foothills. She had a 10 cm bull's eye rash, positive Lyme serology, severe fatigue, polyarthritis resembling RA with extensive rheumatoid nodule formation, cognitive impairment, and exercise intolerance that rendered her disabled. She received antibiotic therapy for 12 months without complete resolution of her symptoms. Minocin is also a recognized treatment for RA. She also gained more than 40 pounds from minocin therapy, a recognized side effect of chronic antibiotic therapy. Plaquenil was added to control rheumatoid nodule formation and minocin was discontinued. Her fatigue and cognitive impairment did not respond to antidepressant therapy. T3 45 ug daily was initiated and was immediately helpful. After 4 weeks of T3 therapy her energy levels returned to normal for the first time in 5 years. She was able to resume her normal activity level and her cognitive impairment resolved. T3 was discontinued and her symptoms gradually returned after 2 months. She now requires only 15 ug of T3 QD with serum T3 levels that are well within the normal range. She is in remission and her rate of nodule formation has also slowed to nearly zero.

It is estimated that there are nearly 16,000 Americans with LD and many are receiving chronic IV antibiotic therapy which is not recognized as an effective therapy by most insurance carriers. Adjunctive therapy that specifically focuses on reversing HDS is effective and relatively inexpensive treatment that alleviates disability and merits further study.

Treatment of Psoriatic Arthritis

Psoriatic arthritis an inflammatory arthritis similar to RA, but with a more asymmetrical distribution of joint involvement, sausage digits, pitted nails, skin lesions (plaques) and systemic features such as iritis that can lead to blindness. It responds to the same medications used for RA, but it can be more resistant to treatment. Unlike RA, psoriatic arthritis can affect the lower spine in the sacroiliac joints leading to complete ankylosis of the joint. For this reason, psoriatic arthritis is considered a spondyloarthropathy (inflammatory disease affecting the spine) along with ankylosing spondylitis, Reiter's syndrome/reactive arthritis, enteropathic arthritis and Becet's.

Example 12

Treatment of a Patient with Psoriatic Arthritis

A 64 year old female presented with a history of psoriasis, psoriatic arthritis, iritis that disfigured both pupils in 1985. She had tried and not tolerated treatment with prednisone, sulfasalazine, methotrexate, and needed additional treatment for erosive arthritis which was deforming her feet and hands. A trial of azothioprine was poorly tolerated due to malaise, methotrexate was tried at low dose and caused nausea, leflunamide also caused nausea and Remicade was initiated. Shortly thereafter, she developed fever of 105 degrees and Remicade was discontinued. 2 months later a trial of T3 30 ug QD was initiated because of fatigue and muscle pain in a Fibromyalgia distribution. Within 6 weeks, her muscle pain had resolved, her psoriatic arthritis was in remission, her psoriatic skin lesions resolved and her energy level increased to 9/10. Five months later her T3 was tapered off and she remained in remission for 3 months. Psoriatic arthritis is known to flare with environmental, physical and emotional stress.

The treatment of HDS in patients with spondyloarthropathies has not previously been described, nor has the use of T3 previously been advocated for the treatment of spondyloarthropathy.

Treatment of Myositis

Myositis is a rare disease that involves tissue-damaging inflammation of the muscle fibers and skin. Myositis is a term that describes several illnesses including polymyositis, dermatomyositis and inclusion body myositis. The symptoms of myositis include severe muscle weakness that can make movement impossible and may require mechanical ventilation when the respiratory muscle are involved. Serum reveals an elevated CPK and sedimentation rate. EMG testing can help identify areas of muscle with abnormal electrical conduction and muscle biopsy confirms the diagnosis, although muscle biopsy is not always diagnostic. Treatment requires prednisone control inflammation, and DMARD therapy is used to minimize the need for long term prednisone therapy. The challenge to treating this condition is to avoid the many disabling side effects associated with chronic prednisone therapy. For this reason, effective alternative therapies to prednisone for myositis are of great interest.

Example 13

Treatment of a Patient with Myositis 67 year old male with bilateral lower extremity weakness and mild upper extremity pain was referred for evaluation of an elevated CPK of 1100 (normal<190 mg/dl). Electrical studies were borderline with some mild abnormalities in the paraspinal musculature. Muscle biopsy was non diagnostic and treatment with prednisone 40 mg QD did not completely resolve his symptoms of fatigue and muscle weakness. CPK levels did return to normal after prednisone and increased when prednisone was tapered. The patient grew weary of the prednisone side effects and discontinued treatment. He was evaluated by a university-based neurologist who specializes in diseases of muscle. The patient was offered treatment that was equally ineffective. He began to show some symptoms of fibromyalgia with severe fatigue, muscle pain and cognitive impairment. His thyroid studies were evaluated and all values were in the normal range. To reverse the HDS component of his condition, a trial of T3 was initiated and within one month his symptoms improved. His T3 dose was gradually increased to 45 ug daily and he reported a complete remission stating "I felt like an 18 year old again playing with my grandkids." His symptoms returned when his dose was tapered to zero, but not to the same degree as pretreatment. In this case, T3 therapy was more effective than prednisone had been with fewer side effects.

Example 14

Treatment of a Patient with Chronic Back Pain

A 72 year old female was referred for evaluation of mildly elevated CPK levels of 250 mg/dl and chronic upper back pain following treatment with a lipid lowering agent known to induce myopathy. Her symptoms had persisted for years despite the discontinuation of the offending medication. Her thyroid studies were evaluated and all values were in the normal range. A trial of T3 was initiated to improve muscle metabolism. Her symptoms gradually improved and her CPK levels dropped to normal over a period of 3 months. She reported improved energy levels and cognitive function as well as resolution of her chronic upper back pain.

It appears that treating the HDS component of inflammatory disease with T3 may provide an effective alternative for the treatment of myositis with prednisone.

Treatment of Scleroderma

Scleroderma is a potentially life threatening condition with few effective therapies. It is a condition associated with thickening, hardening, or tightening of the skin, blood vessels and internal organs. There are two types of scleroderma:
(1) localized scleroderma affecting the skin as morphia (hard, oval shaped patches on the skin) or linear (lines or streaks of thickened skin in areas such as the arms, legs or forehead) and (2) generalized scleroderma affect many parts of the body.

There are two types of generalized scleroderma:
a.) Limited scleroderma occurs gradually and affects the skin of the hands and later may affect the esophagus, lungs or intestines.

b.) Diffuse scleroderma develops more suddenly, with skin thickening throughout the body. Internal organs are more affected and this condition is often lethal.

Scleroderma is primarily diagnosed by physical exam, although serologic studies can be helpful. The positive anti-centromere antibody test is often positive in localized scleroderma and the SCL 70 is often positive for those with diffuse scleroderma. Unfortunately, there is no cure for Scleroderma and patients may develop worsening circulation problems leading to finger and toe gangrene and amputation, or lung or heart fibrosis that is progressive and lethal. Innovative treatment approaches include proastacyclin analogues to control pulmonary artery hypertension, and cyclophosphamide infusion to control pulmonary fibrosis. Neither treatment is curative. The clinical findings of Raynaud's syndrome (finger blood vessel constriction) frequently accompany Scleroderma, and T3 has been used to treat Raynaud's in the past with some success. During dormancy there is lower than normal peripheral circulation to minimize heat loss and these findings are consistent with Scleroderma. Additionally, the abnormal fibrosis seen in scleromyxedema is not unlike fibrotic changes seen in patients with some forms of thyroid disease. Low fT3 and elevated rT3 is a feature of HDS and it produces a state that is similar to hypothyroidism. Alterations or reversal of the hand fibrosis seen in patients with scleroderma following treatment with T3 has not been described.

Example 15

Treatment of a Patient with Scleroderma

A 37-year old male with worsening sclerodactyly of his hands and wrists presented to the clinic for evaluation and treatment. He was unable to play guitar or practice martial arts due to worsening finger range of motion restrictions. His thyroid studies revealed an elevated TSH of 8 IU/ml consistent with hypothyroidism and he was placed on T4 (thyroxine). His energy level improved but his finger range of motion was not affected. He also had (+) Lyme studies and after a second opinion at a university-based clinic, treatment for Lyme disease was recommended and administered. His grip strength and range of motion remained disabling. Six months later, there was no indication of improvement and a trial of T3 was prescribed. His finger range of motion gradually improved and he was able to return to his guitar playing and martial arts with only mild restrictions. T3 was discontinued and T4 was reinstituted. His condition remained stable and his energy level remains excellent until he underwent a course of cortisone from another clinician. Cortisone is known to increase rT3 and lower fT3 levels. His energy level and grip were compromised by the cortisone for greater than 3 months and he returned for treatment with T3. His condition responded to another course of T3.

Example 16

Treatment of a Patient with Scleroderma II

A 59 year old female with localized scleroderma involving her hands and with scleromyxedema involving her shins described worsening lower extremity weakness impairing her ability to ascend stairs. She also displayed some features of lupus with a history of pleural effusion, malar rash and a positive ANA. Her CPK was elevated to 700 mg/dl and a course of prednisone and methotrexate were prescribed. She did not tolerate prednisone therapy, although it decreased her CPK level and improved muscle strength. Her scleromyxedema improved on methotrexate therapy. She had a long-standing history of hypothyroidism and was receiving T4 therapy with normal labs. Reverse T3 levels were elevated to the upper limit of normal and fT3 was in the lower limits of normal making a ratio of rT3 to fT3 of greater than 10 indicating a compromised peripheral conversion of T4 to T3. A trial of T3 improved her energy level and maintained her CPK in the normal range as did the previous course of prednisone. Her scleromyxedema seemed to respond to the T3 as well with additional resolution of symptoms beyond that seen with methotrexate. A medication error occurred and her disease flared requiring ER attention for sever chest pain and shortness of breath. Labs for autoimmune activation were positive, however, thyroid studies revealed an elevated TSH consistent with under-treated hypothyroidism. Two days of corticosteroid were prescribed and her T4 dose was increased to address the hypothyroidism. Her symptoms again remitted and remained controlled when the corticosteroid was withdrawn.

A link between thyroid disease and autoimmune disease has been described, but a flare of lupus-like pleuritis attributable to inadequate thyroid replacement is not an expected finding. The adjunctive use of T3 as DMARD therapy for scleroderma may provide further improvement. T3 increases nitric oxide synthetase activity, which improves peropheral circulation and increases prostacyclin synthetase activity, which may reverse pulmonary artery hypertension is also important for treatment of scleroderma. That T3 therapy improved finger range of motion and apparently reduced the severity of sclerodactyly is especially noteworthy. Addressing the HDS component of autoimmune disease appears to offer a significant advance to current treatment protocols Treatment of Reflex Sympathetic Dystrophy (RSD)

Reflex sympathetic dystrophy involves a disturbance in the sympathetic nervous system, which controls the opening and closing blood vessels or sweat glands. It primarily affects the hands and feet. RSD often develops after a trauma to an area followed by changes in the sympathetic control of that area. Commonly patients with RSD describe burning, painful or swollen limbs, temperature changes and changes in skin color, rapid hair or nail growth. Eventually the tissues may become retracted or weakened. It is seen in association with surgery, diabetes, thyroid disorders, lung disease, infections, heart attack or stroke. Treatment options are limited to biofeedback, blood pressure medications, physical therapy, nerve blocks or surgical nerve transactions. This condition is often chronic and often leads to disability.

Example 17

Treatment of a Patient with Fibromyalgia and RSD

A 37-year old female presented for treatment of Fibromyalgia and was found to have severe RSD involving the left foot and shin. She was barely able to use the clutch in her car because even the slightest pressure is pain inducing and walking was difficult. Foot discoloration was reported and textbook photographs of RSD were identical to the appearance of her lower extremity. A trial of T3 30 ug QDis initiated for treatment of her fibromyalgia and within 3 weeks her RSD is 90% resolved. Her symptoms of RSD remain in remission after she was weaned from a 2 month course of T3 therapy.

Any potential treatment for RSD represents a boon and the rapid normalization of sympathetic activity to her peripheral nerves with T3 is worthy of further study. RSD may be a manifestation of dormancy since control of blood flow to the periphery is critical to survival. There may be a protective mechanism to alter blood flow and pain sensitivity to injured limbs during dormancy. The sympathetic hyperactivity is a finding that is common to dormancy and RSD.

REFERENCES

1.) Legakis I N, Golematis B C, Dourakis N, Lymberopoulou I, Mountokalakis T, Leandros E A. Low T3 syndrome with asynchronous changes of TT3 and rT3 values in laparoscopic cholecystectomy. Endocr Res. 1998 May; 24(2): 205-13.
2.) Chikenji T, Mizutani M, Kitsukawa Y. Anaesthesia, not surgical stress, induces increases in serum concentrations of reverse triiodothyronine and thyroxine during surgery. Exp Clin Endocrinol. 1990 April; 95(2):217-23.

3.) Pineda G, Aguayo J, Ribalta J, Gonzalez M, Reyes H. [Thyroid function tests in normal pregnant women (third trimester) and in pregnant women with pregnancy cholestasis or with acute hepatitis] Rev Med Chil. 2000 January; 128(1):35-43.

4.) Roti E, Minelli R, Salvi M. Thyroid hormone metabolism in obesity. Int J Obes Relat Metab Disord. 2000 June; 24 Suppl 2:S113-5.

5.) McCormack P D, Thomas J, Malik M, Staschen C M. Cold stress, reverse T3 and lymphocyte function. Alaska Med. 1998 July-September; 40(3):55-62.

6.) Hashimoto H, Igarashi N, Miyawaki T, Sato T. Effects of tumor necrosis factor-alpha, interleukin-1 beta, and interleukin-6 on type I iodothyronine 5'-deiodination in rat thyroid cell line, FRTL-5. J Interferon Cytokine Res. 1995 April; 15(4):367-75.

7.) Shiroky J B, Cohen M, Ballachey M L, Neville C. Thyroid dysfunction in rheumatoid arthritis: a controlled prospective survey. Ann Rheum Dis. 1993 June; 52(6):454-6

7.1.) Ijuin T, Douchi T, Yamamoto S, Ijuin Y, Nagata Y. The relationship between maternity blues and thyroid dysfunction. J Obstet Gynaecol Res. 1998 February; 24(1):49-55.

7.2.) Champagne F, Meaney M J. Like mother, like daughter: evidence for non-genomic transmission of parental behavior and stress responsivity. Prog Brain Res. 2001; 133:287-302.

7.3.) Tyson, Peter. Secrets of Hibernation. NOVA website download. 2001:p. 3

7.4.) Grigg G, Beard L. Hibernation by echidnas in mild climates: hints about the evolution of endothermy? Life in the Cold. Springer Press 2000:5-19

7.5.) Nichol S, Andersen N. Patterns of hibernation of echidnas in Tasmania. Life in the Cold. Springer Press 2000:21-8.

8.) Moldofsky H, et. al. Musculosketal symptoms and non-REM sleep disturbance in patients with "fibrositis syndrome" and healthy subjects. Psychosom Med. 1975 July-August; 37(4):341-51

9.) Wolfe F, Cathey M A, Kleinheksel S M. Fibrositis (Fibromyalgia) in rheumatoid arthritis. J Rheumatol. 1984 December; 11(6):814-8.

10.) Wolfe F, Smythe H A, Yunus M B, Bennett R M, Bombardier C, Goldenberg D L, Tugwell P, Campbell S M, Abeles M, Clark P, et al. The American College of Rheumatology 1990 Criteria for the Classification of Fibromyalgia. Report of the Multicenter Criteria Committee. Arthritis Rheum. 1990 February; 33(2):160-72.

11.) Smythe H A, Moldofsky H. Two contributions to understanding of the "fibrositis" syndrome. Bull Rheum Dis. 1977-78; 28(1):928-31

12.) Mellman T A, Bustamante V, Fins A I, Pigeon W R, Nolan B. REM sleep and the early development of posttraumatic stress disorder. Am J Psychiatry. 2002 October; 159(10):1696-701

13.) Berlant J, van Kammen D P. Open-label topiramate as primary or adjunctive therapy in chronic civilian posttraumatic stress disorder: a preliminary report. J Clin Psychiatry. 2002 January; 63(1):15-20.

14.) Gillin J C, Smith-Vaniz A, Schnierow B, Rapaport M H, Kelsoe J, Raimo E, Marler M R, Goyette L M, Stein M B, Zisook S. An open-label, 12-week clinical and sleep EEG study of nefazodone in chronic combat-related posttraumatic stress disorder. J Clin Psychiatry. 2001 October; 62(10):789-96

15.) Hudson J I, Mangweth B, Pope H G Jr, De Col C, Hausmann A, Gutweniger S, Laird N M, Biebl W, Tsuang M T. Family study of affective spectrum disorder. Arch Gen Psychiatry. 2003 February; 60(2):170-7.

16.) Chang L, Mayer E A, Johnson T, FitzGerald L Z, Naliboff B. Differences in somatic perception in female patients with irritable bowel syndrome with and without fibromyalgia. Pain. 2000 February; 84(2-3):297-307.

17.) Lydiard R B. Irritable bowel syndrome, anxiety, and depression: what are the links? J Clin Psychiatry. 2001; 62 Suppl 8:38-45; discussion 46-7.

18.) Kendall-Tackett K A. Physiological correlates of childhood abuse: chronic hyperarousal in PTSD, depression, and irritable bowel syndrome. Child Abuse Negl. 2000 June; 24(6):799-810.

19.) Neeck, G., Crofford, L J. Neuroendocrine pertubations in FM & CFS. Rheum Disease Clin of North Amer. 26; 4: 989-1002

20.) Okifuji A, Turk D C. Stress and psychophysiological dysregulation in patients with fibromyalgia syndrome. Appl Psychophysiol Biofeedback. 2002 June; 27(2):129-41.

21.) Griep E N, Boersma J W, Lentjes E G, Prins A P, van der Korst J K, de Kloet E R. Function of the hypothalamic-pituitary-adrenal axis in patients with fibromyalgia and low back pain. J Rheumatol. 1998 July; 25(7):1374-81.

22.) Demitrack M A, Crofford L J. Evidence for and pathophysiologic implications of hypothalamic-pituitary-adrenal axis dysregulation in fibromyalgia and chronic fatigue syndrome. Ann N Y Acad Sci. 1998 May 1; 840:684-97.

23.) Oquendo M A, Echavarria G, Galfalvy H C, Grunebaum M F, Burke A, Barrera A, Cooper T B, Malone K M, John Mann J. Lower cortisol levels in depressed patients with comorbid post-traumatic stress disorder. Neuropsychopharmacology. 2003:28(3):591-8.

24.) Rinne T, de Kloet E R, Wouters L, Goekoop J G, de Rijk R H, van den Brink W. Fluvoxamine reduces responsiveness of HPA axis in adult female BPD patients with a history of sustained childhood abuse. Neuropsychopharmacology. 2003 January; 28(1): 126-32.

25.) Rinne T, de Kloet E R, Wouters L, Goekoop J G, DeRijk R H, van den Brink W. Hyperresponsiveness of hypothalamic-pituitary-adrenal axis to combined dexamethasone/corticotropin-releasing hormone challenge in female borderline personality disorder subjects with a history of sustained childhood abuse. Biol Psychiatry. 2002 Dec. 1; 52(11):1102-12.

26.) Marshall R D, Garakani A. Psychobiology of the acute stress response and its relationship to the psychobiology of post-traumatic stress disorder. Psychiatr Clin North Am. 2002 June; 25(2):385-95.

27.) Riedel W, Schlapp U, Leck S, Netter P, Neeck G. Blunted ACTH and cortisol responses to systemic injection of corticotropin-releasing hormone (CRH) in fibromyalgia: role of somatostatin and CRH-binding protein. Ann N Y Acad Sci. 2002 June; 966:483-90.

28.) Riedel W, Layka H, Neeck G. Secretory pattern of GH, TSH, thyroid hormones, ACTH, cortisol, FSH, and LH in patients with fibromyalgia syndrome following systemic injection of the relevant hypothalamic-releasing hormones. Z Rheumatol. 1998; 57 Suppl 2:81-7.

29.) Newport D J, et. al. Cerebrospinal Fluid Corticotropin-Releasing Factor (CRF) and Vasopressin Concentrations Predict Pituitary Response in the CRF Stimulation Test: A Multiple Regression Analysis. Neuropsychopharmacology. 2003 March; 28(3):569-576

30.) Vermetten E, Bremner J D. Circuits and systems in stress. I. Preclinical studies. Depress Anxiety. 2002; 15(3):126-47.
31.) Rasmusson A M, Lipschitz D S, Wang S, Hu S, Vojvoda D, Bremner J D, Southwick S M, Charney D S. Increased pituitary and adrenal reactivity in premenopausal women with posttraumatic stress disorder. Biol Psychiatry. 2001 Dec. 15; 50(12):965-77.
32.) Kizildere S, et. al. During a corticotropin-releasing hormone test in healthy subjects, administration of a beta-adrenergic antagonist induced secretion of cortisol and dehydroepiandrosterone sulfate and inhibited secretion of ACTH. Eur J Endocrinol. 2003 January; 148(1):45-53.
33.) Martinez-Lavin M, Vidal M, Barbosa R E, Pineda C, Casanova J M, Nava A. Norepinephrine-evoked pain in fibromyalgia. A randomized pilot study. BMC Musculoskelet Disord. 2002; 3(1):2.
34) Cohen H, Neumann L, Alhosshle A, Kotler M, Abu-Shakra M, Buskila D. Abnormal sympathovagal balance in men with fibromyalgia. J Rheumatol. 2001 March; 28(3):581-9.
35.) vanOyen Witvliet C. Traumatic intrusive imagery as an emotional memory phenomenon: a review of research and explanatory information processing theories. Clin Psychol Rev. 1997; 17(5):509-36.
36.) Gurguis G N, et. al. Neutrophil beta2-adrenergic receptor coupling efficiency to Gs protein in subjects with posttraumatic stress disorder and normal controls. Psychopharmacology (Berl). 1999 April; 143(2):131-40.
37.) Orr S P, et. al. De novo conditioning in trauma-exposed individuals with and without posttraumatic stress disorder. J Abnorm Psychol. 2000 May; 109(2):290-8.
38.) Grossman D. On killing. II: The psychological cost of learning to kill. Int J Emerg Ment Health. 2001 Summer; 3(3):137-44.
39.) Larson A A, et. al. Changes in the concentrations of amino acids in the cerebrospinal fluid that correlate with pain in patients with fibromyalgia: implications for nitric oxide pathways. Pain. 2000 August; 87(2):201-11.
40.) van West D, Maes M. Neuroendocrine and immune aspects of fibromyalgia. BioDrugs. 2001; 15(8):521-31
41.) Russell I J. The promise of substance P inhibitors in fibromyalgia. Rheum Dis Clin North Am. 2002 May; 28(2):329-42.
42.) Friedman M J. What might the psychobiology of post-traumatic stress disorder teach us about future approaches to pharmacotherapy? J Clin Psychiatry. 2000; 61 Suppl 7:44-51.
43.) Maes M, et. al. Higher serum prolyl endopeptidase activity in patients with posttraumatic stress disorder. J Affect Disord. 1999 April; 53(1):27-34.
44.) Horger B A, Roth R H. The role of mesoprefrontal dopamine neurons in stress. Crit Rev Neurobiol. 1996; 10(3-4):395-418.
45.) Staud R. Evidence of involvement of central neural mechanisms in generating fibromyalgia pain. Curr Rheumatol Rep. 2002 August; 4(4):299-305.
46.) Gracely R H, Petzke F, Wolf J M, Clauw D J. Functional magnetic resonance imaging evidence of augmented pain processing in fibromyalgia. Arthritis Rheum. 2002 May; 46(5): 1333-43.
47.) Staud R, Smitherman M L. Peripheral and central sensitization in fibromyalgia: pathogenetic role. Curr Pain Headache Rep. 2002 August; 6(4):259-66
48.) Raymond I et. al. Incorporation of pain in dreams of hospitalized burn victims. Sleep. 2002 Nov. 1; 25(7):765-70.
49.) Mayer E A, Craske M, Naliboff B D. Depression, anxiety, and the gastrointestinal system. J Clin Psychiatry. 2001; 62 Suppl 8:28-36; discussion 37
50.) Weisberg R B, et. al. Nonpsychiatric illness among primary care patients with trauma histories and posttraumatic stress disorder. Psychiatr Serv. 2002 July; 53(7):848-54.
51.) Allgulander C, Kasper S. Coping with somatic comorbidities: striving for complete recovery. Psychopharmacol Bull. 2002 Summer; 36 Suppl 2:103-11.
52.) Goettl V M, et. al Reduced basal release of serotonin from the ventrobasal thalamus of the rat in a model of neuropathic pain. Pain. 2002 September; 99(1-2):359-66.
53.) Legangneux E, Mora J J, Spreux-Varoquaux O, Thorin I, Herrou M, Alvado G, Gomeni C. Cerebrospinal fluid biogenic amine metabolites, plasma-rich platelet serotonin and [3H]imipramine reuptake in the primary fibromyalgia syndrome. Rheumatology (Oxford). 2001 March; 40(3):290-6.
54.) Butterfield M I, Becker M, Marx C E. Post-traumatic Stress Disorder in Women: Current Concepts and Treatments. Curr Psychiatry Rep. 2002 December; 4(6):474-86.
55.) Strawn J R, Ekhator N N, Anthenelli R M, Baker D G, Maxwell R A, Hill K K, Geracioti T D. Intra- and inter-individual relationships between central and peripheralserotonergic activity in humans: a serial cerebrospinal fluid sampling study. Life Sci. 2002 Jul. 26; 71(10):1219-25.
56.) Seedat S, Stein D J, Ziervogel C, Middleton T, Kaminer D, Emsley R A, Rossouw W. Comparison of response to a selective serotonin reuptake inhibitor in children, adolescents, and adults with posttraumatic stress disorder. J Child Adolesc Psychopharmacol. 2002 Spring; 12(1):37-46.
61.) Bennett R M. Adult growth hormone deficiency in patients with fibromyalgia. Curr Rheumatol Rep. 2002 August; 4(4):306-12.
62.) Moldofsky H. Management of sleep disorders in fibromyalgia. Rheum Dis Clin North Am. 2002 May; 28(2):353-65.
63.) Paiva E S, Deodhar A, Jones K D, Bennett R. Impaired growth hormone secretion in fibromyalgia patients: evidence for augmented hypothalamic somatostatin tone. Arthritis Rheum. 2002 May; 46(5):1344-50.
64.) Bremner J D, Krystal J H, Southwick S M, Charney D S. Noradrenergic mechanisms in stress and anxiety: II. Clinical studies. Synapse. 1996 May; 23(1):39-51.
65.) Anderberg U M, Uvnas-Moberg K. Plasma oxytocin levels in female fibromyalgia syndrome patients. Z Rheumatol. 2000 December; 59(6):373-9.
66.) Samborski W, Stratz T, Schochat T, Mennet P, Muller W. [Biochemical changes in fibromyalgia] Z Rheumatol. 1996 May-June; 55(3):168-73. German.
67.) Teicher M H, Andersen S L, Polcari A, Anderson C M, Navalta C P. Developmental neurobiology of childhood stress and trauma. Psychiatr Clin North Am. 2002 June; 25(2):397-426, vii-viii.
68.) Maes M, Lin A H, Bonaccorso S, Goossens F, Van Gastel A, Pioli R, Delmeire L, Scharpe S. Higher serum prolyl endopeptidase activity in patients with posttraumatic stress disorder. J Affect Disord. 1999 April; 53(1):27-34.
69.) Henry J P, Wang S. Effects of early stress on adult affiliative behavior. Psychoneuroendocrinology. 1998 November; 23 (8): 863-75.
70.) Wang S. Traumatic stress and attachment. Acta Physiol Scand Suppl. 1997; 640:164-9.
71.) Pall M L. Common etiology of posttraumatic stress disorder, fibromyalgia, chronic fatigue syndrome and multiple chemical sensitivity via elevated nitricoxide/peroxynitrite. Med Hypotheses. 2001 August; 57(2): 139-45.

72.) Pall M L, Satterle J D. Elevated nitric oxide/peroxynitrite mechanism for the common etiology of multiple chemical sensitivity, chronic fatigue syndrome, and posttraumatic stress disorder. Ann NY Acad Sci. 2001 March; 933:323-9.

73.) Wik G, Fischer H, Bragee B, Kristianson M, Fredrikson M. Retrosplenial cortical activation in the fibromyalgia syndrome. Neuroreport. 2003 Mar. 24; 14(4):619-21

74.) Gracely R H, Petzke F, Wolf J M, Clauw D J. Functional magnetic resonance imaging evidence of augmented pain processing in fibromyalgia. Arthritis Rheum. 2002 May; 46(5):1333-43.

75.) Kwiatek R, Barnden L, Tedman R, Jarrett R, Chew J, Rowe C, Pile K. Regional cerebral blood flow in fibromyalgia: single-photon-emission computed tomography evidence of reduction in the pontine tegmentum and thalami. Arthritis Rheum. 2000 December; 43(12):2823-33.

76.) Pissiota A, Frans O, Fernandez M, von Knorring L, Fischer H, Fredrikson M. Neurofunctional correlates of posttraumatic stress disorder: a PET symptomprovocation study. Eur Arch Psychiatry Clin Neurosci. 2002 April; 252(2):68-75.

77.) Osuch E A, Benson B, Geraci M, Podell D, Herscovitch P, McCann U D, Post R M. Regional cerebral blood flow correlated with flashback intensity in patients with post-traumatic stress disorder. Biol Psychiatry. 2001 Aug. 15; 50(4):246-53.

78.) Pitman R K, Shin L M, Rauch S L. Investigating the pathogenesis of posttraumatic stress disorder with neuroimaging. J Clin Psychiatry. 2001; 62 Suppl 17:47-54.

79.) Mirzaei S, Knoll P, Keck A, Preitler B, Gutierrez E, Umek H, Kohn H, Pecherstorfer M. Regional cerebral blood flow in patients suffering from post-traumatic stress disorder. Neuropsychobiology. 2001; 43(4):260-4.

80.) Park D C, Glass J M, Minear M, Crofford L J. Cognitive function in fibromyalgia patients. Arthritis Rheum. 2001 September; 44(9):2125-33.

81.) Glass J M, Park D C. Cognitive dysfunction in fibromyalgia. Curr Rheumatol Rep. 2001 April; 3(2):123-7.

82.) Leavitt, F. Cognitive and dissociative manifestations in fibromyalgia. J Clin. Rheum 2002; 8(2):77-84

83.) Stein M B, Kennedy C M, Twamley E W. Neuropsychological function in female victims of intimate partner violence with and without posttraumatic stress disorder. Biol Psychiatry. 2002 Dec. 1; 52(11):1079-88.

84.) Ferguson E, Cassaday H J. Theoretical accounts of Gulf War Syndrome: from environmental toxins to psychoneuroimmunology and neurodegeneration. Behav Neurol. 2001-2002; 13(3-4):133-47.

85.) Orr S P, Metzger L J, Pitman R K. Psychophysiology of post-traumatic stress disorder. Psychiatr Clin North Am. 2002 June; 25(2):271-93.

86.) Horner M D, Hamner M B. Neurocognitive functioning in posttraumatic stress disorder. Neuropsychol Rev. 2002 March; 12(1):15-30.

87.) Cohen H, Neumann L, Alhosshle A, Kotler M, Abu-Shakra M, Buskila D. Abnormal sympathovagal balance in men with fibromyalgia. J Rheumatol. 2001 March; 28(3):581-9.

88.) Bell I R, Baldwin C M, Russek L G, Schwartz G E, Hardin E E. Early life stress, negative paternal relationships, and chemical intolerance in middle-aged women: support for a neural sensitization model. J Womens Health. 1998 November; 7(9):1135-47.

89.) Martinez-Lavin M, Hermosillo A G, Mendoza C, Ortiz R, Cajigas J C, Pineda C, Nava A, Vallejo M. Orthostatic sympathetic derangement in subjects with fibromyalgia. J Rheumatol. 1997 April; 24(4):714-8.

90.) Moldofsky H. Sleep and pain. Sleep Med Rev. 2001 October; 5(5):385-396.

91.) Fitzcharles M A, Costa D D, Poyhia R. A study of standard care in fibromyalgia syndrome: a favorable outcome. J Rheumatol. 2003 January; 30(1):154-9.

92.) Nicassio P M, Moxham E G, Schuman C E, Gevirtz R N. The contribution of pain, reported sleep quality, and depressive symptoms to fatigue in fibromyalgia. Pain. 2002 December; 100(3):271-9.

93.) Ferguson E, Cassaday H J. Theoretical accounts of Gulf War Syndrome: from environmental toxins topsychoneuroimmunology and neurodegeneration. Behav Neurol. 2001-2002; 13(3-4): 133-47.

94.) Taylor R R, Jason L A. Chronic fatigue, abuse-related traumatization, and psychiatric disorders in a community-based sample. Soc Sci Med. 2002 July; 55(2):247-56.

95.) Sansone R A, Gaither G A, Sansone L A. Childhood trauma and adult somatic preoccupation by body area among women in an internal medicine setting: a pilot study. Int J Psychiatry Med. 2001; 31(2):147-54.

96.) Maquet D, Croisier J L, Renard C, Crielaard J M. Muscle performance in patients with fibromyalgia. Joint Bone Spine. 2002 May; 69(3):293-9.

97.) Park J H, Niermann K J, Olsen N. Evidence for metabolic abnormalities in the muscles of patients with fibromyalgia. Curr Rheumatol Rep. 2000 April; 2(2):131-40.

98.) Borman P, Celiker R, Hascelik Z. Muscle performance in fibromyalgia syndrome. Rheumatol Int. 1999; 19(1-2):27-30.

99.) Weisberg R B, Bruce S E, Machan J T, Kessler R C, Culpepper L, Keller M B. Nonpsychiatric illness among primary care patients with trauma histories and posttraumatic stress disorder. Psychiatr Serv. 2002 July; 53(7):848-54.

100.) Hamner M B, Hitri A. Plasma beta-endorphin levels in post-traumatic stress disorder: a preliminary report on response to exercise-induced stress. J Neuropsychiatry Clin Neurosci. 1992 Winter; 4(1):59-63.

101.) Khvatova E M, Samartzev V N, Zagoskin P P, Prudchenko I A, Mikhaleva I I. Delta sleep inducing peptide (DSIP): effect on respiration activity in rat brain mitochondria and stress protective potency under experimental hypoxia. Peptides. 2003 February; 24(2):307-311.

102.) Pongratz D E, Sievers M. Fibromyalgia-symptom or diagnosis: a definition of the position. Scand J Rheumatol Suppl. 2000; 113:3-7.

103.) Pongratz D E, Spath M. Morphologic aspects of fibromyalgia. Z Rheumatol. 1998; 57 Suppl 2:47-51.

104.) McDermid A J, Rollman G B, McCain G A. Generalized hypervigilance in fibromyalgia: evidence of perceptual amplification. Pain. 1996 August; 66(2-3):133-44.

105.) Clauw D J. Potential mechanisms in chemical intolerance and related conditions. Ann N Y Acad Sci. 2001 March; 933:235-53.

106.) Sherman J J, Turk D C, Okifuji A. Prevalence and impact of posttraumatic stress disorder-like symptoms on patients with fibromyalgia syndrome. Clin J Pain. 2000 June; 16(2):127-34.

107.) Mertin P, Mohr P B. Incidence and correlates of post-trauma symptoms in children from backgrounds of domestic violence. Violence Vict. 2002 October; 17(5):555-67.

108.) Norris F H, Weisshaar D L, Conrad M L, Diaz E M, Murphy A D, Lbanez G E. A qualitative analysis of post-traumatic stress among Mexican victims of disaster. J Trauma Stress. 2001 October; 14(4):741-56.

109.) Dalgleish T, Moradi A R, Taghavi M R, Neshat-Doost H T, Yule W. An experimental investigation of hypervigilance for threat in children and adolescents with post-traumatic stress disorder. Psychol Med. 2001 April; 31(3):541-7.

110.) Alfici S, Sigal M, Landau M. Primary fibromyalgia syndrome—a variant of depressive disorder? Psychother Psychosom. 1989; 51(3): 156-61.
111.) 5: Muris P, Merckelbach H, Peeters E. The links between the Adolescent Dissociative Experiences Scale (A-DES), fantasy proneness, and anxiety symptoms. J Nerv Ment Dis. 2003 January; 191(1):18-24.
112.) Malta L S, Blanchard E B, Taylor A E, Hickling E J, Freidenberg B M. Personality disorders and posttraumatic stress disorder in motor vehicle accident survivors. J Nerv Ment Dis. 2002 November; 190(11):767-74.
113.) Brosschot J F, Aarsse H R. Restricted emotional processing and somatic attribution in fibromyalgia. Int J Psychiatry Med. 2001; 31(2):127-46.
114.) Bryant R A, Harvey A G. Gender differences in the relationship between acute stress disorder and posttraumatic stress disorder following motor vehicle accidents. Aust N Z J. Psychiatry. 2003 April; 37(2):226-229.
115.) Gershuny B S, Cloitre M, Otto M W. Peritraumatic dissociation and PTSD severity: do event-related fears about death and control mediate their relation? Behav Res Ther. 2003 February; 41(2):157-66.
116.) Van Houdenhove B, Neerinckx E, Onghena P, Vingerhoets A, Lysens R, Vertommen H. Daily hassles reported by chronic fatigue syndrome and fibromyalgia patients in tertiary care: a controlled quantitative and qualitative study. Psychother Psychosom. 2002 July-August; 71(4): 207-13
117.) Cohen H, Neumann L, Haiman Y, Matar M A, Press J, Buskila D. Prevalence of post-traumatic stress disorder in fibromyalgia patients: Overlapping syndromes or posttraumatic fibromyalgia syndrome? Semin Arthritis Rheum. 2002 August; 32(1):38-50.
118.) Tsigos C, Chrousos G P. Hypothalamic-pituitary-adrenal axis, neuroendocrine factors and stress. J Psychosom Res. 2002 October; 53(4):865-71.
119.) Lee H A, Gabriel R, Bale A J, Bolton P, Blatchley N F. Clinical findings of the second 1000 UK Gulf War veterans who attended the Ministry of Defence's Medical Assessment Programme. J R Army Med Corps. 2001 June; 147 (2):153-60.
120.) Ehlert U, Gaab J, Heinrichs M. Psychoneuroendocrinological contributions to the etiology of depression, post-traumatic stress disorder, and stress-related bodily disorders: the role of the hypothalamus-pituitary-adrenal axis. Biol Psychol. 2001 July-August; 57(1-3): 141-52.
121.) Van Houdenhoven, B et. al. Victimization in chronic fatigue syndrome & fibromyalgia: a controlled study on prevalence and characteristics. Psychosomatics 2001; January-February; 42(1): 21-28 Usually family of origin and correlation not seen in RA and MS patients.
122.) Taylor, M. et. al. The prevalence of sexual abuse in women with FM. Arthritis & Rheum. 1995; 38:2. 229-234
123.) Goldberg, R. et al. Relationship between traumatic events in childhood and chronic pain. Disability & Rehab. 1999; 21:1. 23-30. Harvard study "Child traumatic events are significantly related to chronic pain. Child abuse is broader than physical and sexual abuse."
124.) Finestone H M, Stenn P, Davies F, Stalker C, Fry R, Koumanis J. Chronic pain and health care utilization in women with a history of childhood sexual abuse. Child Abuse Negl. 2000 April; 24(4):547-56.
125.) Mathilde, H et. al. Sexual and physical abuse in women with FM. Arthritis & Rheum. 1995; 38:2.235-241.
126.) Kreidler M C, Briscoe L A, Beech R R. Pharmacology for post-traumatic stress disorder related to childhood sexual abuse: a literature review. Perspect Psychiatr Care. 2002 October-December; 38(4):135-45.
127.) Bifulco A, Moran P M, Baines R, Bunn A, Stanford K. Exploring psychological abuse in childhood: II. Association with other abuse and adult clinical depression. Bull Menninger Clin. 2002 Summer; 66(3):241-58.
128.) Lekander M, Fredrikson M, Wik G. Neuroimmune relations in patients with fibromyalgia: a positron emission tomography study. Neurosci Lett. 2000 Mar. 24; 282(3): 193-6.
129.) Hernanz W, Valenzuela A, Quijada J, Garcia A, de la Iglesia J L, Gutierrez A, Povedano J, Moreno I, Sanchez B. Lymphocyte subpopulations in patients with primary fibromyalgia. J Rheumatol. 1994 November; 21(11):2122-4.
130.) Jara L J, Lavalle C, Fraga A, Gomez-Sanchez C, Silveira L H, Martinez-Osuna P, Germain B F, Espinoza L R. Prolactin, immunoregulation, and autoimmune diseases. Semin Arthritis Rheum. 1991 April; 20(5):273-84.
131.) Inoue-Sakurai C, Maruyama S, Morimoto K. Posttraumatic stress and lifestyles are associated with natural killer cell activity in victims of the Hanshin-Awaji earthquake in Japan. Prev Med. 2000 November; 31(5):467-73.
131.1.) Lyman C P, Willis J S, Malan A, Wang L C H. Hibernation and Torpor in Mammals and Birds. Academic Press 1982:pp 1-31.
131.2.) Kayser Ch. The Physiology of Natural Hibernation. Pergamon Press 1961. pp 1-44.
131.3.) Harlow H J, Lohuis T, Beck T, Iaizze P. Muscle strength in overwintering bears. Nature Feb. 22, 2001(409):997.
131.4.) Sterling, J. Polar Bears. Ann Arbor: University of Michigan Press, 1988.
131.5.) Hissa R, Siekkinen J, Hohtola E, Saarela S, Hakala A, Pudas J. Seasonal patterns in the physiology of the European brown bear (*Ursus arctos arctos*) in Finland. Comp Biochem Physiol A Physiol. 1994 November; 109(3):781-91.
131.6.) Muller A E. Aspects of social life in the fat-tailed dwarf lemur (*Cheirogaleus medius*): inferences from body weights and trapping data. Am J Primatol. 1999 November; 49(3):265-80.
131.7) Kohrle J, Schomburg L, Drescher S, Fekete E, Bauer K. Rapid stimulation of type I 5'-deiodinase in rat pituitaries by 3,3',5-triiodo-L-thyronine. Mol Cell Endocrinol. 1995 Feb. 27; 108(1-2):17-21.
131.8.) Altshuler L L, Bauer M, Frye M A, Gitlin M J, Mintz J, Szuba M P, Leight K L, Whybrow P C. Does thyroid supplementation accelerate tricyclic antidepressant response? A review and meta-analysis of the literature. Am J Psychiatry. 2001 October; 158(10):1617-22.
131.9) Brzezinska-Slebodzinska E, Slebodzinski A B, Styczynska E. Stimulatory effect of melatonin on the 5'-monodeiodinase activity in the liver, kidney, and brown adipose tissue during the early neonatal period of the rabbit. J Pineal Res. 1998 April; 24(3):137-41.
132.1) Nedvidkova J, Papezova H, Haluzik M, Schreiber V. Interaction between serum leptin levels and hypothalamo-hypophyseal-thyroid axis in patients with anorexia nervosa. Endocr Res. 2000 May; 26(2):219-30.
132.2) Bianco A C, Nunes M T, Hell N S, Maciel R M. The role of glucocorticoids in the stress-induced reduction of extrathyroidal 3,5,3'-triiodothyronine generation in rats. Endocrinology. 1987 March; 120(3): 1033-8.

145.) Baumgartner A, Hiedra L, Pinna G, Eravci M, Prengel H, Meinhold H. Rat brain type II 5'-iodothyronine deiodinase activity is extremely sensitive to stress. J Neurochem. 1998 August; 71(2):817-26.

146.) Eravci M, Pinna G, Meinhold H, Baumgartner A. Effects of pharmacological and nonpharmacological treatments on thyroid hormone metabolism and concentrations in rat brain. Endocrinology. 2000 March; 141(3):1027-40.

147.) 1: Everson C A, Nowak T S Jr. Hypothalamic thyrotropin-releasing hormone mRNA responses to hypothyroxinemia induced by sleep deprivation. Am J Physiol Endocrinol Metab. 2002 July; 283(1):E85-93.

148.) Burr W A, Ramsden D B, Griffiths R S, Black E G, Hoffenberg R, Meinhold H, Wenzel K W. Effect of a single dose of dexamethasone on serum concentrations of thyroid hormones. Lancet. 1976 Jul. 10; 2(7976):58-61.

149.) Schlienger J L, Kauffmann J P, Bur F, Sapin R, Demangeat C, Hollender L F. [Effect of surgery on the level of total and free thyroid hormones, reverse T3 and TSH] Ann Endocrinol (Paris). 1982 July-September; 43(4):259-68. French.

150.) Johansson G, Laakso M L, Karonen S L, Peder M. Examination stress affects plasma levels of TSH and thyroid hormones differently in females and males. Psychosom Med. 1987 July-August; 49(4):390-6.

151.) Vitek V, Shatney C H. Thyroid hormone alterations in patients with shock and injury. Injury. 1987 September; 18(5):336-41.

152.) Langer P, Balazova E, Vician M, Martino E, Jezova D, Michalikova S, Moravec R. Acute development of low T3 syndrome and changes in pituitary-adrenocortical function after elective cholecystectomy in women: some differences between young and elderly patients. Scand J Clin Lab Invest. 1992 May; 52(3):215-20.

153.) Torpy D J, Tsigos C, Lotsikas A J, Defensor R, Chrousos G P, Papanicolaou D A. Acute and delayed effects of a single-dose injection of interleukin-6 on thyroid function in healthy humans. Metabolism. 1998 October; 47(10):1289-93.

154.) Cerillo A G, Sabatino L, Bevilacqua S, Farneti P A, Scarlattini M, Forini F, Glauber M. Nonthyroidal illness syndrome in off-pump coronary artery bypass grafting. Ann Thorac Surg. 2003 January; 75(1):82-7.

155.) Joosten K F, de Kleijn E D, Westerterp M, de Hoog M, Eijck F C, Hop W C J, Voort E V, Hazelzet J A, Hokken-Koelega A C. Endocrine and metabolic responses in children with meningoccocal sepsis: striking differences between survivors and nonsurvivors. J Clin Endocrinol Metab. 2000 October; 85(10):3746-53.

156.) Shigematsu H, Shatney C H. [The effect of triiodothyronine (T3) and reverse triiodothyronine (rT3) on canine hemorrhagic shock] Nippon Geka Gakkai Zasshi. 1988 October; 89(10):1587-93. Japanese.

157.) Kales J D, Kales A. Nocturnal psychophysiological correlates of somatic conditions and sleep disorders. Int J Psychiatry Med. 1975; 6(1-2):43-62.

158.) Carpenter A C, Timiras P S. Sleep organization in hypo- and hyperthyroid rats. Neuroendocrinology. 1982 June; 34(6):438-43.

159.) Goto S, Billmire D F, Grosfeld J L. Hypothyroidism impairs colonic motility and function. An experimental study in the rat. Eur J Pediatr Surg. 1992 February; 2(1):16-21.

160.) Lake-Bakaar G. Hypothyroidism and functional bowel disease. Am J. Med. 1990 March; 88(3):312-3.

161.) Meserve L A, Leathem J H. Development of hypothalamic-pituitary-adrenal response to stress in rats made hypothyroid by exposure to thiouracil from conception. J Endocrinol. 1981 September; 90(3):403-9

162.) Ban Y, Ban Y, Taniyama M, Hara H, Abe T, Katagiri T. Aberrant luteinizing hormone-releasing hormone-stimulated adrenocorticotropichormone secretion in a patient with pituitary hyperplasia due to primary hypothyroidism. Endocr J. 2000 August; 47(4):481-6.

163.) Tohei A, Watanabe G, Taya K. Hypersecretion of corticotrophin-releasing hormone and arginine vasopressin in hypothyroid male rats as estimated with push-pull perfusion. J Endocrinol. 1998 February; 156(2):395-400.

164.) Tohei A, Akai M, Tomabechi T, Mamada M, Taya K. Adrenal and gonadal function in hypothyroid adult male rats. J Endocrinol. 1997 January; 152(1):147-54.

165.) Fommei E, Iervasi G. The role of thyroid hormone in blood pressure homeostasis: evidence from short-term hypothyroidism in humans. J Clin Endocrinol Metab. 2002 May; 87(5): 1996-2000.

166.) Foley C M, McAllister R M, Hasser E M. Thyroid status influences baroreflex function and autonomic contributions to arterial pressure and heart rate. Am J Physiol Heart Circ Physiol. 2001 May; 280(5):H2061-8.

167.) Savard P, Blanchard L M, Merand Y, Bedard P, Dussault J H, Dupont A. Influences of both thyroid and bovine growth hormones on substance P,thyrotropin-releasing hormone, serotonin and 5-hydroxyindoleacetic acid contents in the lumbar spinal cord of developing rats. Brain Res. 1984 March; 315(1):105-10.

168.) Aronin N, Coslovsky R, Chase K. Hypothyroidism increases substance P concentrations in the heterotopic anteriorpituitary. Endocrinology. 1988 June; 122(6):2911-4.

169.) Jones P M, Ghatei M A, Steel J, O'Halloran D, Gon G, Legon S, Burrin J M, Leonhardt U, Polak J M, Bloom S R. Evidence for neuropeptide Y synthesis in the rat anterior pituitary and the influence of thyroid hormone status: comparison with vasoactive intestinal peptide, substance P, and neurotensin. Endocrinology. 1989 July; 125(1):334-41.

170.) Bauer M, Heinz A, Whybrow P C. Thyroid hormones, serotonin and mood: of synergy and significance in the adult brain. Mol Psychiatry. 2002; 7(2):140-56.

171.) Badaue-Passos D Jr, Ventura R, Silva L F, Olivares E L, Reis L C. Effect of brain serotoninergic stimulation on sodium appetite of euthyroid and hypothyroid rats. Exp Physiol. 2003 March; 88(Pt 2):251-60.

172.) Moreno B, Rodriguez-Manzaneque J C, Perez-Castillo A, Santos A. Thyroid hormone controls the expression of insulin-like growth factor I receptor gene at different levels in lung and heart of developing and adult rats. Endocrinology. 1997 March; 138(3):1194-203.

173.) Brown M R, Parks J S, Adess M E, Rich B H, Rosenthal I M, Voss T C, VanderHeyden T C, Hurley D L. Central hypothyroidism reveals compound heterozygous mutations in the Pit-1 gene. Horm Res. 1998; 49(2):98-102.

174.) Adan R A, Cox J J, van Kats J P, Burbach J P. Thyroid hormone regulates the oxytocin gene. J Biol Chem. 1992 Feb. 25; 267(6):3771-7.

175.) Dellovade T L, Zhu Y S, Pfaff D W. Thyroid hormones and estrogen affect oxytocin gene expression in hypothalamic neurons. J Neuroendocrinol. 1999 January; 11(1):1-10.

176.) Colin I M, Kopp P, Zbaren J, Haberli A, Grizzle W E, Jameson J L. Expression of nitric oxide synthase III in human thyroid follicular cells: evidence for increased expression in hyperthyroidism. Eur J Endocrinol. 1997 June; 136(6):649-55.

177.) Quesada A, Sainz J, Wangensteen R, Rodriguez-Gomez I, Vargas F, Osuna A. Nitric oxide synthase activity in hyperthyroid and hypothyroid rats. Eur J Endocrinol. 2002 July; 147(1):117-22.

178.) Constant E L, de Volder A G, Ivanoiu A, Bol A, Labar D, Seghers A, Cosnard G, Melin J, Daumerie C. Cerebral blood flow and glucose metabolism in hypothyroidism: a positron emission tomography study. J Clin Endocrinol Metab. 2001 August; 86(8):3864-70.

179.) Kinuya S, Michigishi T, Tonami N, Aburano T, Tsuji S, Hashimoto T. Reversible cerebral hypoperfusion observed with Tc-99m HMPAO SPECT irreversible dementia caused by hypothyroidism. Clin Nucl Med. 1999 September; 24(9):666-8.

180.) Baldini I M, Vita A, Mauri M C, Amodei V, Carrisi M, Bravin S, Cantalamessa L Psychopathological and cognitive features in subclinical hypothyroidism. Prog Neuropsychopharmacol Biol Psychiatry. 1997 August; 21(6):925-35.

181.) Ganguli M, Burmeister L A, Seaberg E C, Belle S, DeKosky S T. Association between dementia and elevated TSH: a community-based study. Biol Psychiatry. 1996 Oct. 15; 40(8):714-25.

182.) Lambert M, Thissen J P, Doyen C, Col J, Coche E. Orthostatic hypotension associated with hypothyroidism. Acta Clin Belg. 1984; 39(1):48-50

183.) Morrow L B. How thyroid disease presents in the elderly. Geriatrics. 1978 April; 33(4):42-5.

184.) Hylander B, Ekelund L G, Rosenqvist U. The cardiovascular response at rest and during exercise in hypothyroid subjects to thyroxine substitution. Clin Cardiol. 1983 March; 6(3):116-24.

185.) Enriquez J A, Fernandez-Silva P, Garrido-Perez N, Lopez-Perez M J, Perez-Martos A, Montoya J. Direct regulation of mitochondrial RNA synthesis by thyroid hormone. Mol Cell Biol. 1999 January; 19(1):657-70.

186.) Martinez B, del Hoyo P, Martin M A, Arenas J, Perez-Castillo A, Santos A. Thyroid hormone regulates oxidative phosphorylation in the cerebral cortex andstriatum of neonatal rats. J Neurochem. 2001 September; 78(5):1054-63.

187.) Sasaki N, Takahashi A, Nakano N, Saito T. [A case of 'hallucination of soliloquy' with hypothyroidism induced Hashimotodisease. Meaning of psychopathological research about symptomatic psychosis] Seishin Shinkeigaku Zasshi. 2001; 103(2):185-96. Japanese.

188.) Dorn L D, Burgess E S, Dichek H L, Putnam F W, Chrousos G P, Gold P W. Thyroid hormone concentrations in depressed and nondepressed adolescents: group differences and behavioral relations. J Am Acad Child Adolesc Psychiatry. 1996 March; 35(3):299-306.

189.) Simon N M, Blacker D, Korbly N B, Sharma S G, Worthington J J, Otto M W, Pollack M H. Hypothyroidism and hyperthyroidism in anxiety disorders revisited: new data and literature review. J Affect Disord. 2002 May; 69(1-3):209-17.

190.) Provinciali M, Muzzioli M, Di Stefano G, Fabris N. Recovery of spleen cell natural killer activity by thyroid hormone treatment in old mice. Nat Immun Cell Growth Regul. 1991; 10(4):226-36

191.) Marsh J A, Merlino P G, Staeheli P. The effects of triodothyronine and thymulin on avian NK cytolytic activity. Int Immunopharmacol. 2001 September; 1(9-10):1823-30.

192.) Haraldsen L, Soderstrom-Lauritzsen V, Nilsson G E. Oxytocin stimulates cerebral blood flow in rainbow trout (*Oncorhynchus mykiss*) through a nitric oxide dependent mechanism. Brain Res. 2002 Mar. 1; 929(1):10-4.

193.) Young L J, Lim M M, Gingrich B, Insel T R. Cellular mechanisms of social attachment. Horm Behav. 2001 September; 40(2):133-8.

194.) Altemus M, deuster P, Galliven E, Carter C S, Gold P. Suppression of hypothalamic-pituitary-adrenal axis responses to stress in lactating women. J of Clin Endocrin. 1995:80(10):2954-59.

195.) Buck M, Squire T, Andrews M. Coordinate expression of the PDK4 gene: a means of regulating fuel selection in a hibernating mammal. Physiol Genomics 8; 5-13, 2002

196.) Kilduff T S, Krilowics B, Milsom W K, Trachsel L, Wang L C H. Sleep and mammalian Hibernation: Homolous adaptations and homolous processes?. Sleep, 16(4):372-386.

197.) Deboer T, Tobler I. The djungarian hamster is sleep deprived during daily torpor. Life in the Cold. Springer Press 2000: pp 251-260.

198.) Saitongdee P, Milner P, Loesch A, Knight G, Burnstock G. Electron-immunocytochemical studies of perivascular nerves of mesenteric and renal arteries of golden hamsters during and after arousal from hibernation. J Anat. 1999 July; 195 (Pt 1):121-30.

199.) Taguchi T, Ikeda K, Shono T, Goto S, Kubota M, Kawana T, Hirose R, Toyohara T. Autonomic innervation of the intestine from a baby with megacystis microcolon intestinal hypoperistalsis syndrome: I. Immunohistochemical study. J Pediatr Surg. 1989 December; 24(12):1264-6.

200.) Shinomura Y, Himeno S, Kurokawa M, Takahashi S, Kuroshima T, Okuno M, Kanayama S, Tsuji K, Higashimoto Y, Tarui S. Release of vasoactive intestinal peptide by intraduodenal infusion of HCl or fat and intramuscular injection of neostigmine in man. Hepatogastroenterology. 1985 June; 32(3):129-32.

INDUSTRIAL APPLICABILITY

Embodiments of this invention are useful in the health care, research, veterinary medicine, medical research and the pharmaceutical industries. New normal ranges are provided for detecting abnormalities of energy metabolism and aiding in diagnosis of human dormancy syndrome. By providing normal ranges that reflect individuals not suffering from dormancy syndrome, abnormalities can be more easily detected. Treatments based upon identification of a new normal range can be more appropriate, and can be provided to individuals previously considered to be normal, but in fact, have disorders including human dormancy syndrome.

I claim:

1. A method for treating a patient, comprising:
   (a) measuring serum levels of rT3 and fT3;
   (b) calculating the ratio of rT3/fT3, wherein said ratio is above about 4; and
   (c) determining the presence of one or more findings of human dormancy syndrome (HDS) selected from the group consisting of autoimmune disease, systemic lupus erythematosus, rheumatoid arthritis, post-Lyme disease, myositis, psoriatic arthritis, decreased mitochondrial membrane permeability, scleroderma, reflex sympathetic dystrophy, dementia and post-traumatic stress disorder; and
   (d) administering T3 to decrease the ratio of serum rT3/fT3 to below about 4 and said finding returns substantially to normal.

2. The method of claim 1, further comprising at least one therapy selected from the group consisting of physical therapy and occupational therapy.

3. The method of claim 1, further comprising at least one therapy selected from the group consisting of psychotherapy, cognitive behavioral therapy, exposure therapy, beta-adrenergic antagonist therapy, serotonin reuptake inhibitor therapy, $MgSO_4$ therapy, magnesium therapy, oxytocin therapy, dopamine increasing therapy, glucocorticoid therapy, ACTH therapy, and nitric oxide enhancing therapy.

4. The method of claim 1, further comprising nitric oxide enhancing therapy.

5. The method of claim 1, further comprising administering a pharmaceutical agent selected from the group consisting of melatonin, testosterone, oxytocin, selenium, iodine, magnesium and nitroglycerine.

6. The method of claim 1, further comprising stimulating the enzyme 5'-D1 to increase T3 production so that the ratio of serum rT3/fT3 decreases to below about 4.

7. The method of claim 1, further comprising inhibiting the enzyme 5-D1 and stimulating at least one of the enzymes 5'-D2 and 5'-D1 so that the ratio of serum rT3/fT3 is below about 4.

8. The method of claim 1 wherein said dementia is associated with Alzheimer's disease.

9. The method of claim 1, wherein said improvement is assessed using dementia rating scale-2 ("DMS-2").

10. The method of claim 1, further comprising administering a serotonin re-uptake inhibitor.

11. The method of claim 10, wherein said serotonin re-uptake inhibitor is (±)fluoxetine, fluvoxamine, paroxetine, sertaline, (±) venlafaxine, or St. John's Wort.

* * * * *